United States Patent [19]

Serban et al.

[11] 4,248,619

[45] Feb. 3, 1981

[54] BIS[PYRIMIDYLOXY(THIO)]BENZENE DERIVATIVES

[75] Inventors: Alexander Serban, Doncaster; Keith G. Watson, Box Hill North; Richard B. Warner, Ringwood, all of Australia

[73] Assignee: ICI Australia Limited, Melbourne, Australia

[21] Appl. No.: 60,634

[22] Filed: Jul. 23, 1979

[30] Foreign Application Priority Data

Aug. 8, 1978 [AU] Australia .............................. PD5409
Aug. 8, 1978 [AU] Australia .............................. PD5412

[51] Int. Cl.$^3$ .................... A01N 43/54; C07D 405/12
[52] U.S. Cl. .......................................... 71/92; 544/296
[58] Field of Search ............................. 544/296; 71/92

[56] References Cited

FOREIGN PATENT DOCUMENTS

| | | |
|---|---|---|
| 1187 | 3/1979 | European Pat. Off. . |
| 2360581 | 3/1978 | France . |
| 109170 | 10/1974 | German Democratic Rep. . |
| 42-9474 | 5/1967 | Japan .......................................... 71/92 |
| 775370 | 5/1957 | United Kingdom ..................... 544/296 |

*Primary Examiner*—Paul M. Coughlan, Jr.
*Attorney, Agent, or Firm*—Cushman, Darby & Cushman

[57] ABSTRACT

The invention concerns novel compounds of the formula I

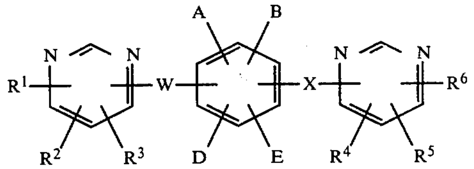

I wherein W and X are independently chosen from oxygen and sulfur. The compounds are herbicides and in further embodiments the invention provides: herbicidal compositions containing as active ingredient a compound of formula I; processes for severely damaging or killing unwanted plants by applying to the plants or to the growth medium of the plants an effective amount of a compound of formula I; and processes for the synthesis of compounds of formula I.

22 Claims, No Drawings

BIS[PYRIMIDYLOXY(THIO)]BENZENE DERIVATIVES

This invention relates to herbicidal pyrimidine compounds, to herbicidal compositions and processes utilizing such compounds and to the synthesis of such compounds We have found that certain bis(pyrimidyloxy) benzenes, bis(pyrimidylthio)benzenes and pyrimidyloxypyrimidylthiobenzes and derivatives thereof exhibit useful herbicidal activity.

Accordingly we provide a process of inhibiting the growth of, severely damaging, or killing plants which process comprises applying to the plant or the growth medium thereof an effective amount of a composition comprising as active ingredient a compound of formula I:

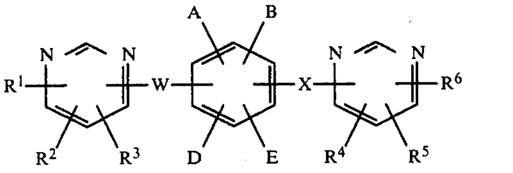

I wherein A, B, D and E are independently chosen from the group consisting of hydrogen, halogen, nitro, cyano, thiocyano, formyl, optionally substituted alkyl, optionally substituted alkenyl, optionally substituted cycloalkyl, optionally substituted alkylcarbonyl, optionally substituted amino, optionally substituted phenyl, optionally substituted carbamoyl, sulfo, alkoxysulfonyl, optionally substituted sulfamoyl and the groups YR and $$\overset{O}{\overset{\|}{C}}YR$$

wherein Y is oxygen or sulfur and R is chosen from the group consisting of hydrogen, optionally substituted alkyl, optionally substituted alkenyl, optionally substituted alkynyl, optionally substituted cycloalkyl, optionally substituted acyl, optionally substituted alkoxycarbonyl, optionally substituted phenyl and the cation of an inorganic or organic base, or two adjacent substituents chosen from A, B, D and E form a 1,3-butadienylene bridging group;

$R^1$, $R^2$, $R^3$, $R^4$, $R^5$ and $R^6$ are independently chosen from the group consisting of hydrogen, halogen, hydroxy, nitro, cyano, thiocyano, optionally substituted alkyl, optionally substituted alkenyl, optionally substituted alkoxy, optionally substituted alkenyloxy, optionally substituted alkynyloxy, optionally substituted alkylthio, optionally substituted cycloalkyl, optionally substituted amino, optionally substituted phenyl, carboxy, alkoxycarbonyl, optionally substituted carbamoyl, sulfo, alkoxysulfonyl and optionally substituted sulfamoyl; W and X are independently chosen from oxygen and sulfur; or an optical isomer thereof; or a tautomer thereof; or a salt thereof; and a carrier therefor.

Suitable $R^1$, $R^2$, $R^3$, $R^4$, $R^5$ and $R^6$ include hydrogen, halogen, nitro, cyano, thiocyano, carboxy and sulfo; $C_1$ to $C_6$ alkyl, $C_2$ to $C_6$ alkenyl, $C_1$ to $C_6$ alkoxy, $C_2$ to $C_6$ alkenyloxy, $C_2$ to $C_6$ alkynyloxy and $C_1$ to $C_6$ alkylthio wherein each group is optionally substituted with one or two substituents chosen from halogen, phenyl, hydroxy, and $C_1$ to $C_6$ alkoxy; $C_3$ to $C_7$ cycloalkyl optionally substituted with one or two $C_1$ to $C_4$ alkyl groups; $NR^7R^8$ wherein $R^7$ and $R^8$ are independently chosen from hydrogen, $C_1$ to $C_6$ alkyl, $C_2$ to $C_6$ alkanoyl, phenyl and benzoyl; $NR^9R^{10}R^{11}]^{\oplus}X^{\ominus}$ wherein $X^{\ominus}$ is an anion and $R^9$, $R^{10}$ and $R^{11}$ are chosen independently from $C_1$ to $C_6$ alkyl optionally substituted with one or two substituents chosen from halogen, phenyl, hydroxy and $C_1$ to $C_6$ alkoxy, and phenyl optionally substituted with one or two substituents chosen from halogen, $C_1$ to $C_6$ alkyl, $C_1$ to $C_6$ alkoxy, nitro and cyano; $C_1$ to $C_6$-(alkoxy)carbonyl; $C_1$ to $C_6$-(alkoxy)sulfonyl; carbamoyl and sulfamoyl optionally substituted on the amide nitrogen with one or two groups chosen from $C_1$ to $C_6$ alkyl and phenyl optionally substituted with one or two substituents chosen from halogen, $C_1$ to $C_6$ alkyl, $C_1$ to $C_6$ alkoxy, nitro and cyano; and phenyl optionally substituted with one or two substituents chosen from halogen, $C_1$ to $C_6$ alkyl, $C_1$ to $C_6$ alkoxy, nitro and cyano.

Suitable A, B, D and E include hydrogen, halogen, nitro, cyano, thiocyano and sulfo; $C_1$ to $C_{12}$ alkyl and $C_2$ to $C_6$ alkenyl wherein each group is optionally substituted with one or two substituents chosen from halogen, phenyl, hydroxy, $C_2$ to $C_6$ alkoxycarbonyl and $C_1$ to $C_6$ alkoxy; $C_3$ to $C_7$ cycloalkyl optionally substituted with one or two $C_1$ to $C_4$ alkyl groups; $C_2$ to $C_6$ alkylcarbonyl; $NR^7R^8$ and $NR^9R^{10}R^{11}]^{\oplus}X^{\ominus}$ wherein $R^7$, $R^8$, $R^9$, $R^{10}$, $R^{11}$ and $X^{\ominus}$ are as hereinbefore defined; phenyl optionally substituted with one or two substituents chosen from halogen, $C_1$ to $C_6$ alkyl, $C_1$ to $C_6$ alkoxy, nitro and cyano; carbamoyl and sulfamoyl optionally substituted on the amide nitrogen with one or two groups chosen from $C_1$ to $C_6$ alkyl and phenyl optionally substituted with one or two substituents chosen from halogen, $C_1$ to $C_6$ alkyl, $C_1$ to $C_6$ alkoxy, nitro and cyano; $C_1$ to $C_6$ (alkoxy)sulfonyl; a 1,3-butadienylene group wherein two adjacent substituents chosen from A, B, D and E form a bridging group; and the groups YR and $$\overset{O}{\overset{\|}{C}}YR.$$

Suitable R include hydrogen; $C_1$ to $C_{10}$ alkyl, $C_2$ to $C_{10}$ alkenyl and $C_2$ to $C_{10}$ alkynyl wherein each group is optionally substituted with one or two substituents chosen from halogen, phenyl, hydroxy and $C_1$ to $C_6$ alkoxy; $C_3$ to $C_7$ cycloalkyl optionally substituted with one or two $C_1$ to $C_4$ alkyl groups; $C_1$ to $C_6$ alkanoyl; benzoyl optionally substituted on the phenyl ring with one or two substituents chosen from halogen, nitro, cyano, $C_1$ to $C_6$ alkyl and $C_1$ to $C_6$ alkoxy; phenyl optionally substituted with one or two substituents chosen from halogen, $C_1$ to $C_6$ alkyl, $C_1$ to $C_6$ alkoxy, nitro and cyano; the cation of an inorganic base such as, for example, an alkali metal ion or an alkaline earth metal ion; the cation of an organic base such as, for example, an ammonium ion $NR^{12}R^{13}R^{14}R^{15}]^{\oplus}$ wherein $R^{12}$, $R^{13}$, $R^{14}$ and $R^{15}$ are independently chosen from the group hydrogen, $C_1$ to $C_6$ alkyl, $C_1$ to $C_6$ hydroxyalkyl, phenyl and benzyl; and the groups $$-\overset{O}{\overset{\|}{C}}-CH=CH-CO_2H,\ \overset{O}{\overset{\|}{-}}(CH_2)_n-NR_2{}^{16},$$

-continued $-\overset{O}{\overset{\|}{C}}-(CH_2)_n-\overset{\oplus}{N}R_3{}^{16}X^{\ominus}$, $-(CH_2-CHR^{17}O)_m-R^{16}$ and $-\overset{O}{\overset{\|}{C}}-CH=CR_2{}^{16}$ wherein $R^{16}$ is hydrogen or a $C_1$ to $C_6$ alkyl group, $R^{17}$ is hydrogen or methyl, n is an integer from 2 to 6, m is an integer from 2 to 20 and $X^{\ominus}$ is an anion.

Preferred $R^1$, $R^2$, $R^3$, $R^4$, $R^5$ and $R^6$ include hydrogen, halogen, $C_1$ to $C_6$ alkyl, $C_1$ to $C_6$ haloalkyl, nitro, cyano, $C_2$ to $C_6$ alkenyl and phenyl optionally substituted with halogen.

Preferred A, B, D and E include hydrogen, halogen, nitro, cyano, formyl, carbamoyl, $C_1$ to $C_{12}$ alkyl, $C_1$ to $C_6$ haloalkyl, $C_2$ to $C_6$ alkenyl optionally substituted with $C_2$ to $C_6$ alkoxycarbonyl, $C_2$ to $C_6$ alkylcarbonyl, OR wherein R is chosen from $C_1$ to $C_6$ alkyl, $C_2$ to $C_6$ alkenyl, $C_2$ to $C_6$ alkynyl and the groups phenyl and benzyl wherein in each group the phenyl ring is optionally substituted with one or two substituents independently chosen from nitro and halogen; or two adjacent substituents chosen from A, B, D, and E form a 1,3-butadienylene bridging group.

Preferred W and X are oxygen.

Preferred compounds for use in the process of the invention are the bis(2-pyrimidyl) compounds of formula II

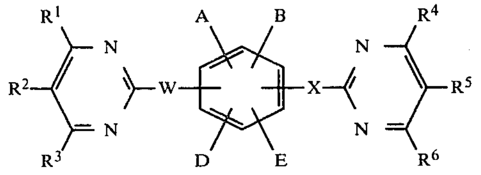

II, the bis(4-pyrimidyl) compounds of formula III

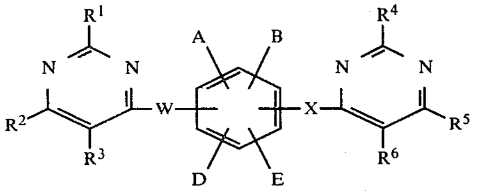

III and the (2-pyrimidyl)-(4-pyrimidyl) compounds of formula IV

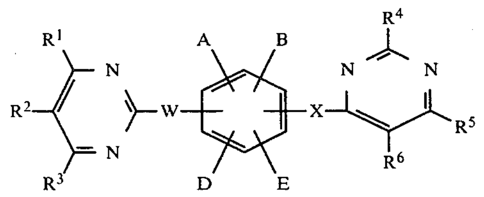

IV wherein:

- $R^1$, $R^2$, $R^3$, $R^4$, $R^5$ and $R^6$ are independently chosen from hydrogen, halogen, $C_1$ to $C_6$ alkyl, $C_1$ to $C_6$ haloalkyl and phenyl optionally substituted with halogen;
- A, B, D and E are independently chosen from hydrogen, halogen, nitro, cyano, carbamoyl, $C_1$ to $C_6$ alkyl, $C_1$ to $C_6$ haloalkyl, $C_2$ to $C_6$ alkenyl, $C_2$ to $C_6$ alkylcarbonyl and OR wherein R is chosen from $C_1$ to $C_6$ alkyl, $C_2$ to $C_6$ alkenyl, $C_2$ to $C_6$ alkynyl and phenyl optionally substituted with one or two nitro groups; and W and X are both oxygen.

Particularly preferred compounds for use in the process of the invention are the bis(2-pyrimidyl) compounds of formula IIa

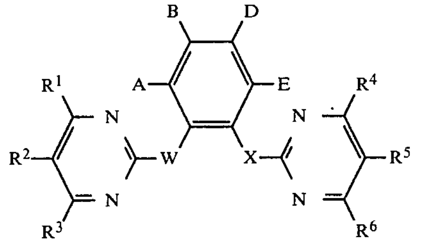

IIa; and the bis(2-pyrimidyl) compounds of formula IIb

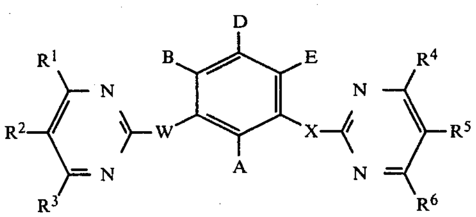

IIb wherein:

- $R^1$, $R^3$, $R^4$ and $R^6$ are hydrogen;
- $R^2$ and $R^5$ are independently chosen from halogen;
- A, B, D and E are independently chosen from hydrogen, halogen, nitro, cyano, $C_1$ to $C_6$ alkyl, $C_2$ to $C_6$ alkenyl and OR wherein R is chosen from $C_1$ to $C_6$ alkyl, $C_2$ to $C_6$ alkenyl, $C_2$ to $C_6$ alkynyl and the groups phenyl and benzyl wherein in each group the phenyl ring is optionally substituted with one or two groups independently chosen from halogen and nitro; and
- W and X are both oxygen.

Those compounds of use in the method of the invention which have a basic functional group may be applied in the form of an acid addition salt. Suitable acid addition salts may be prepared from organic or inorganic mineral acids such as, for example, hydrochloric acid, hydrobromic acid, sulphuric acid, phosphoric acid, maleic acid, acetic acid, nitric acid, benzoic acid, citric acid, succinic acid, malic acid and the like.

Those compounds of use in the method of the invention which have an acidic functional group may be applied in the form of a base addition salt. Suitable base addition salts may be prepared from organic and inorganic bases such as, for example, mono-, di- and triethanolamines and the alkali metal and alkaline earth metal hydroxides and carbonates.

Examples of the types of compounds embraced by the invention include:

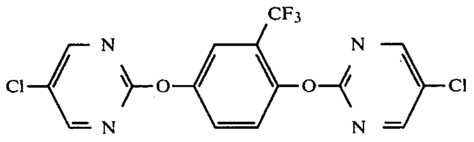

3

-continued

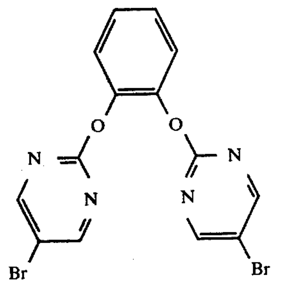

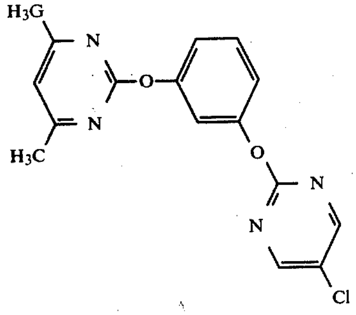

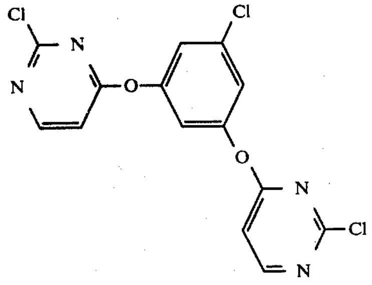

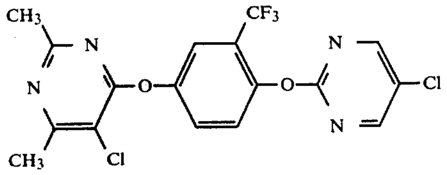

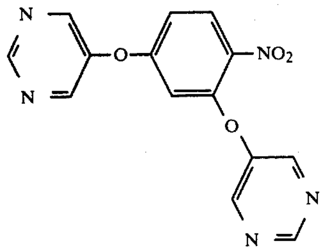

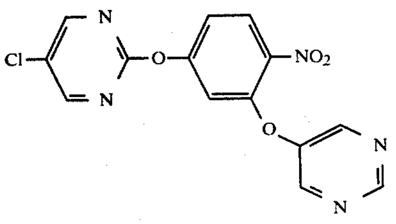

-continued

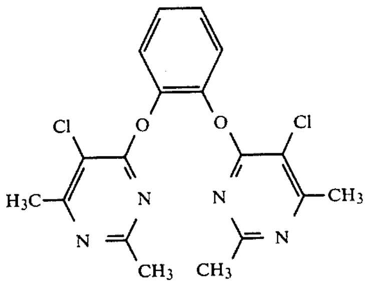

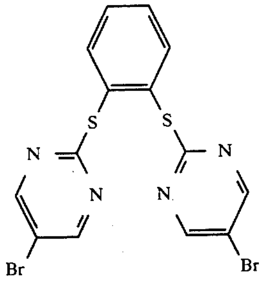

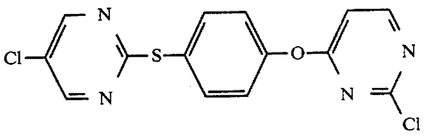

The compounds of formula I, as hereinbefore defined, which may be used in the process of the invention are novel compounds. Accordingly, in a further embodiment the invention provides a compound of formula I

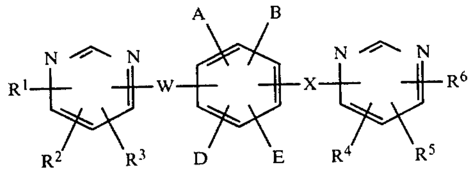

I wherein:

$R^1$, $R^2$, $R^3$, $R^4$, $R^5$ and $R^6$ are independently chosen from the group consisting of hydrogen, halogen, nitro, cyano, thiocyano, carboxy, sulfo; the groups $C_1$ to $C_6$ alkyl, $C_2$ to $C_6$ alkenyl, $C_1$ to $C_6$ alkoxy, $C_2$ to $C_6$ alkenyloxy, $C_2$ to $C_6$ alkynyloxy and $C_1$ to $C_6$ alkylthio wherein each group is optionally substituted with one or more substituents chosen from halogen, phenyl, hydroxy and $C_1$ to $C_6$ alkoxy; $C_3$ to $C_7$ cycloalkyl optionally substituted with one or two $C_1$ to $C_4$ alkyl groups; $NR^7R^8$ wherein $R^7$ and $R^8$ are independently chosen from hydrogen, $C_1$ to $C_6$ alkyl, $C_2$ to $C_6$ alkanoyl, phenyl and benzoyl; $NR^9R^{10}R^{11}]^{\oplus}X^{\ominus}$ wherein $X^{\ominus}$ is an anion and $R^9$, $R^{10}$ and $R^{11}$ are independently chosen from $C_1$ to $C_6$ alkyl optionally substituted with one or two substituents chosen from halogen, phenyl, hydroxy and $C_1$ to $C_6$ alkoxy, and phenyl optionally substituted with one or two substituents chosen from halogen, $C_1$ to $C_6$ alkyl, $C_1$ to $C_6$ alkoxy, nitro and cyano; $C_1$ to $C_6$-(alkoxy)carbonyl; $C_1$ to $C_6$-(alkoxy)sulfonyl; carbamoyl and sulfamoyl optionally substituted on the amide nitrogen with one or two groups chosen from $C_1$ to $C_6$ alkyl and phenyl optionally substituted with one or two substituents chosen from halogen, $C_1$ to $C_6$ alkyl, $C_1$ to $C_6$ alkoxy, nitro and cyano; and phenyl optionally substituted with one or two substituents chosen from halogen, $C_1$ to $C_6$ alkyl, $C_1$ to $C_6$ alkoxy, nitro and cyano;

A, B, D and E are independently chosen from the group consisting of hydrogen, halogen, nitro, cyano, thiocyano, sulfo; the groups $C_1$ to $C_{12}$ alkyl and $C_2$ to $C_6$ alkenyl wherein each group is optionally substituted with one or two substituents chosen from halogen, phenyl, hydroxy, $C_2$ to $C_6$ alkoxycarbonyl and $C_1$ to $C_6$ alkoxy; $C_3$ to $C_7$ cycloalkyl optionally substituted with one or two $C_1$ to $C_4$ alkyl groups; $C_2$ to $C_6$ alkylcarbonyl; $NR^7R^8$ and $NR^9R^{10}R^{11}]^{\oplus}X^{\ominus}$ wherein $R^7$, $R^8$, $R^9$, $R^{10}$, $R^{11}$ and $X^{\ominus}$ are as hereinbefore defined; phenyl optionally substituted with one or two substituents chosen from halogen, $C_1$ to $C_6$ alkyl, $C_1$ to $C_6$ alkoxy, nitro and cyano; carbamoyl and sulfamoyl optionally substituted on the amide nitrogen with one or two groups chosen from $C_1$ to $C_6$ alkyl and phenyl optionally substituted with one or two substituents chosen from halogen, $C_1$ to $C_6$ alkyl, $C_1$ to $C_6$ alkoxy, nitro and cyano; $C_1$ to $C_6$ alkoxysulfonyl; the groups YR and $$\overset{O}{\overset{\|}{C}}YR$$

wherein:

Y is oxygen or sulfur and R is chosen from the group consisting of hydrogen; the groups $C_1$ to $C_{10}$ alkyl, $C_2$ to $C_{10}$ alkenyl and $C_2$ to $C_{10}$ alkynyl wherein each group is optionally substituted with one or two substituents chosen from halogen, phenyl, hydroxy and $C_1$ to $C_6$ alkoxy; the group $C_3$ to $C_7$ cycloalkyl optionally substituted with one or two $C_1$ to $C_4$ alkyl groups; $C_1$ to $C_6$ alkanoyl; benzoyl optionally substituted on the phenyl ring with one or two substituents chosen from halogen, nitro, cyano, $C_1$ to $C_6$ alkyl and $C_1$ to $C_6$ alkoxy; phenyl optionally substituted with one or two substituents chosen from halogen, $C_1$ to $C_6$ alkyl, $C_1$ to $C_6$ alkoxy, nitro and cyano; an alkali metal ion or an alkaline earth metal ion; the group $NR^{12}R^{13}R^{14}R^{15}]^{\oplus}$ wherein $R^{12}$, $R^{13}$, $R^{14}$ and $R^{15}$ are independently chosen from hydrogen, $C_1$ to $C_6$ alkyl, $C_1$ to $C_6$ hydroxyalkyl, phenyl and benzyl; and the groups $$-\overset{O}{\overset{\|}{C}}-CH=CH-CO_2H,\ -\overset{O}{\overset{\|}{C}}-(CH_2)_n-NR_2^{16},$$

$$-\overset{O}{\overset{\|}{C}}-(CH_2)_n-\overset{\oplus}{N}R_3^{16}X^{\ominus},$$

$$\left(CH_2-CHR^{17}O\right)_mR^{16} \text{ and } -\overset{O}{\overset{\|}{C}}-CH=CR_2^{16}$$

wherein $R^{16}$ is hydrogen or $C_1$ to $C_6$ alkyl, $R^{17}$ is hydrogen or methyl, n is an integer from 2 to 6, m is an integer from 2 to 20 and $X^{\ominus}$ is an anion;

or two adjacent substituents chosen from A, B, D and E form a 1,3-butadienylene bridging group;

W and X are independently chosen from oxygen and sulfur; or an optical isomer thereof; or a tautomer thereof or a salt thereof.

Specific examples of the novel compounds of the invention are detailed in the following Tables 1 to 5 inclusive.

TABLE 1

Compounds of Formula IIa

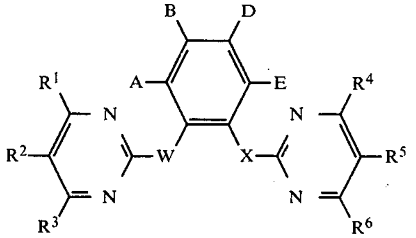

IIa

| Compound No | $R^1$ to $R^{6*}$ | A, B, D, and E* | W | X |
|---|---|---|---|---|
| 4 | $R^2=R^5=Cl$ | All H | O | O |
| 12 | $R^2=R^5=Br$ | All H | O | O |
| 14 | $R^2=R^5=Cl$ | $B = CH_3$ | O | O |
| 19 | $R^2=R^5=Cl$ | $B + D = -CH=CH-CH=CH-$ | O | O |
| 15 | $R^2=R^5=Cl$ | $B = C(CH_3)_3$ | O | O |
| 20 | $R^1=R^3=R^4=R^6=CH_3$ | All H | O | O |
| 22 | $R^1=R^3=R^4=R^6=CCl_3$ | All H | O | O |
| 23 | $R^2=R^5=Cl$ | $B = C_2H_5$ | O | O |
| 24 | $R^2=R^5=Br$ | $B = C_2H_5$ | O | O |
| 25 | $R^2=Cl$, $R^5=Br$ | All H | O | O |
| 26 | $R^2=Cl$, $R^5=Br$ | $D = C_2H_5$ | O | O |
| 27 | $R^2=R^5=Br$ | $B = CH_3$ | O | O |
| 32 | $R^2=R^5=Cl$ | $A = CH_2CH=CH_2$ | O | O |
| 33 | $R^2=R^5=Cl$ | All H | O | S |
| 34 | $R^2=R^5=Cl$ | B = CHO | O | O |
| 36 | $R^2=R^5=Cl$ | $B = CHCl_2$ | O | O |
| 37 | $R^2=R^5=I$ | All H | O | O |
| 39 | $R^2=R^5=Cl$ | $B = NO_2$ | O | O |
| 40 | $R^2=R^5=Cl$ | $B = CH_2CH(Br)CH_3$ | O | O |
| 41 | $R^2=R^5=Cl$ | A = CHO | O | O |
| 42 | $R^2=R^5=Cl$ | $A = CH_3$ | O | O |
| 45 | $R^2=R^5=Cl$ | B = Br | O | O |
| 47 | $R^2=R^5=Cl$ | B = Cl | O | O |

TABLE 1-continued

Compounds of Formula IIa

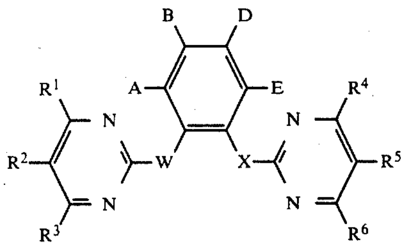

IIa

| Compound No | $R^1$ to $R^6$* | A, B, D, and E* | W | X |
|---|---|---|---|---|
| 48 | $R^2$=$R^5$=Cl | B = $CH_2CH$=$CH_2$ | O | O |
| 49 | $R^2$=$R^5$=Cl | A = $OCH_3$ | O | O |
| 50 | $R^2$=$R^5$=Cl | B = $C_{12}H_{25}$ | O | O |
| 51 | $R^2$=$R^5$=Br | B = Cl | O | O |
| 55 | $R^2$=$R^5$=4-$ClC_6H_4$ | All H | O | O |
| 57 | $R^2$=$R^5$=Cl | B = CN | O | O |
| 58 | $R^2$=$R^5$=Cl | B = CH=$CHCO_2C_2H_5$ | O | O |
| 59 | $R^2$=$R^5$=Cl | A = 4-$ClC_6H_4CH_2O$ | O | O |
| 63 | $R^2$=$R^5$=Cl | A = 2,4-$(NO_2)_2C_6H_3O$ | O | O |
| 66 | $R^2$=$R^5$=Cl | A = $OCH_2CH$=$CH_2$ | O | O |
| 67 | $R^2$=$R^5$=Cl | A = $OCH_2C$≡CH | O | O |
| 71 | $R^1$=$R^3$=$R^4$=$R^6$=$CH_3$ | B = $CH_3$ | O | O |
| 73 | $R^1$=$R^3$=$R^4$=$R^6$=$CH_3$ | B + D = —CH=CH—CH=CH— | O | O |

*Substituents are hydrogen unless otherwise indicated.

TABLE 2

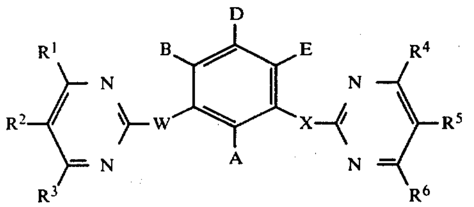

IIb

| Compound No | $R^1$ to $R^6$* | A, B, D and E* | W | X |
|---|---|---|---|---|
| 2 | $R^2$=$R^5$=Cl | All H | O | O |
| 5 | $R^2$=Cl, $R^4$=$R^6$=$CH_3$ | All H | O | O |
| 6 | $R^1$=$R^3$=$R^4$=$R^6$=$CH_3$ | All H | O | O |
| 7 | $R^2$=$R^5$=Cl | D = Cl | O | O |
| 8 | $R^2$=$R^5$=$CH_3$ | All H | O | O |
| 9 | All H | All H | O | O |
| 10 | $R^2$=$R^5$=Br | All H | O | O |
| 11 | $R^1$=$R^4$=$CCl_3$ | All H | O | O |
| 16 | $R^2$=$R^5$=Cl | B = $NO_2$ | O | O |
| 21 | $R^2$=$R^5$=$CF_3$ | All H | O | O |
| 28 | $R^2$=$R^5$=Cl | A = $CH_3$ | O | O |
| 29 | $R^2$=$R^5$=Cl | All H | S | O |
| 30 | $R^2$=$R^5$=Cl | B = $COCH_3$ | O | O |
| 31 | $R^2$=$R^5$=Cl | All H | S | S |
| 46 | $R^2$=$R^5$=Cl | B = $C_2H_5$ | O | O |
| 52 | $R^2$=$R^5$=Br | A = $CH_3$ | O | O |
| 53 | $R^2$=$R^5$=Cl | B = Cl | O | O |
| 54 | $R^2$=$R^5$=Cl | A = $NO_2$ | O | O |
| 60 | $R^2$=$R^5$=$CH_3$ | B = Cl | O | O |
| 61 | $R^2$=$R^5$=Cl | B = $CONH_2$ | O | O |
| 62 | $R^2$=$R^5$=$CH_3$ | B = $C_2H_5$ | O | O |
| 64 | $R^2$=$R^5$=$CH_3$ | D = Cl | O | O |
| 65 | $R^2$=$R^5$=$C_2H_5$ | All H | O | O |
| 68 | $R^2$=$R^5$=$CH_3$ | A = $CH_3$ | O | O |
| 69 | $R^1$=$R^3$=$R^4$=$R^6$=$CH_3$ | All H | O | O |
| 72 | $R^1$=$R^3$=$R^4$=$R^6$=$CH_3$ | B = E = Br | O | O |
| 43 | $R^1$=$R^3$=$R^4$=$R^6$=$CH_3$ | B = E = Cl | O | O |

*Substituents are hydrogen unless otherwise indicated.

TABLE 3

Compounds of Formula IIc

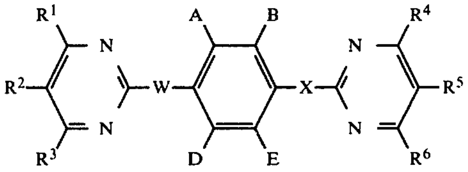

IIc

| Compound No | $R^1$ to $R^6$* | A, B, D and E* | W | X |
|---|---|---|---|---|
| 1 | $R^2$=$R^5$=Cl | All H | O | O |
| 3 | $R^2$=$R^5$=Cl | A = $CF_3$ | O | O |
| 13 | $R^2$=$R^5$=Cl | A = $NO_2$ | O | O |
| 17 | $R^2$=$R^5$=Cl | A = Cl | O | O |
| 18 | $R^2$=$R^5$=Cl | A = $CH_3$ | O | O |
| 44 | $R^1$=$R^3$=$R^4$=$R^6$=$CH_3$ | A = E = Cl | O | O |
| 70 | $R^1$=$R^3$=$R^4$=$R^6$=$CH_3$ | All H | O | O |

*Substituents are hydrogen unless otherwise indicated

TABLE 4

Compounds of Formula IIIa

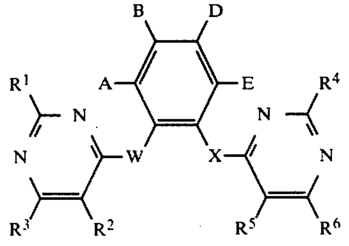

| Compound No | $R^1$ to $R^6$* | A, B, D and E* | W | X |
|---|---|---|---|---|
| 74 | $R^1$=$R^3$=$R^4$=$R^6$=$CH_3$ | All H | O | O |
| 75 | $R^3$=$R^6$=Cl | All H | O | O |
| 77 | $R^1$=$R^4$=Cl | All H | O | O |
| 78 | $R^3$=$R^6$=Cl | B = Cl | O | O |

TABLE 4-continued

Compounds of Formula IIIa

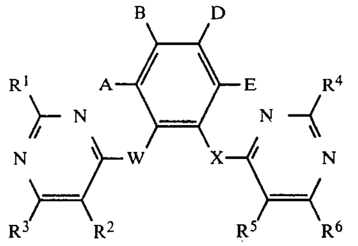

| Compound No | $R^1$ to $R^6$* | A, B, D and E* | W | X |
|---|---|---|---|---|
| 81 | $R^2{=}R^5{=}NO_2, R^3{=}R^6{=}Cl$ | All H | O | O |

*Substituents are hydrogen unless otherwise indicated.

TABLE 5

Miscellaneous Compounds of Formula I

| Compound No | Structure |
|---|---|
| 76 | 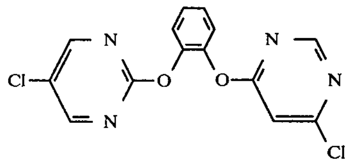 |
| 79 | 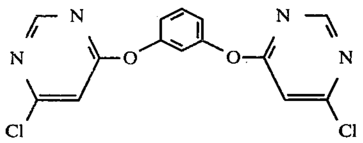 |
| 80 | 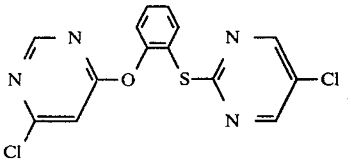 |

The novel compounds of the invention may be prepared by a number of processes. Thus, in yet a further embodiment the invention provides processes for the preparation of novel compounds of formula I. Suitable processes comprise:

(a) Reaction of a pyrimidine derivative of formula X with a pyrimidine of formula XI wherein $R^1$ to $R^6$, A, B, D, E, W and X are as hereinbefore defined and L is a leaving group (e.g. alkylsulfonyl, chlorine, bromine or iodine), according to SCHEME A;

(b) Reaction of a pyrimidine derivative of formula XII with a pyrimidine of formula XIII wherein $R^1$ to $R^6$, A, B, D, E, W and X are as hereinbefore defined and L is a leaving group (e.g. alkylsulfonyl, chlorine, bromine or iodine), according to SCHEME B;

(c) Reaction of a pyrimidine of formula XIV with a dihydroxybenzene, dimercaptobenzene or mercaptophenol of formula XV wherein $R^1$, $R^2$, $R^3$, A, B, D, E, W and X are as hereinbefore defined and L is a leaving group (e.g. alkylsulfonyl, chlorine, bromine or iodine) to give a bis(pyrimidyl) compound of formula Ia, according to SCHEME C.

SCHEME A

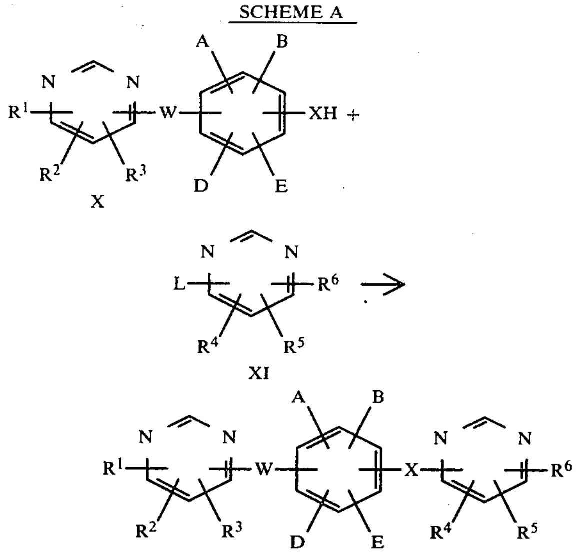

X

XI

I

SCHEME B

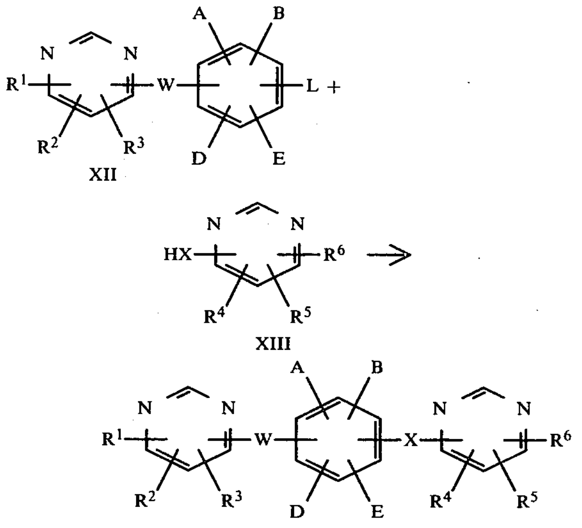

XII

XIII

I

SCHEME C

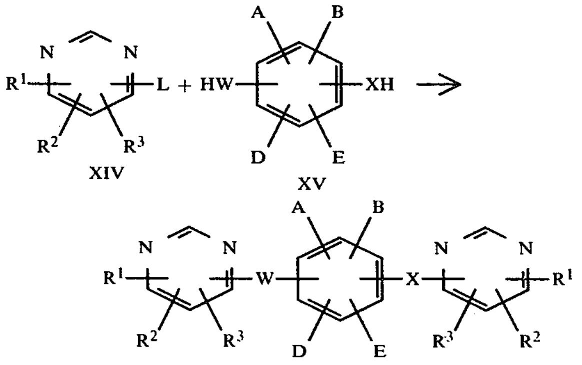

XIV

XV

Ia

The condensation reactions illustrated in SCHEMES A to C outlined above preferably are carried out in the presence of an alkaline material and preferably in the presence of a solvent. Suitable alkaline materials include, for example, the alkali and alkaline earth metal hydroxides and carbonates such as sodium hydroxide, potassium hydroxide, sodium carbonate and potassium carbonate. Suitable solvents include ketones such as, for example, acetone, methyl ethyl ketone and methyl isobutyl ketone, and dipolar aprotic solvents such as, for example, dimethylformamide, dimethylacetamide, dimethylsulfoxide, N-methylpyrrolidone, hexamethylphosphoramide and sulfolan.

The reaction conditions required to effect the condensation reactions illustrated in SCHEMES A to C and outlined above vary according to the nature of the reactants, the alkaline material and the solvent used. In general the reactions are facilitated by the application of heat and usually a reaction temprature in the range of 40° to 150° C. and reaction time of between 0.5 and 20 hours is satisfactory. However, high or lower reaction temperatures and/or shorter or longer reaction times may be used if desired.

Compounds of formula I wherein one or more of A, B, D and E is the group YR and R is hydrogen may be prepared from the corresponding compounds of formula I, wherein R is an optionally substituted alkyl group, by dealkylation. Compounds of formula I wherein one or more of A, B, D and E is the group YR and R is hydrogen may also be prepared from the corresponding compounds of formula I wherein R is an acyl group, by hydrolytic cleavage of the acyl group.

Compounds of formula I wherein one or more of A, B, D and E is the group $$\overset{O}{\overset{\|}{C}}OH$$

may be prepared from the corresponding compounds of formula I wherein one or more of A, B, D and E is the group $$\overset{O}{\overset{\|}{C}}YR$$

wherein R is not hydrogen, by hydrolytic cleavage.

The dealkylation reaction outlined above may be effected using a variety of reagents known in the art. For example, aryl-alkyl ethers may be cleaved using reagents such as pyridine hydrochloride, hydriodic acid, hydrobromic acid, sodium thioethoxide in dimethylformamide, acetyl p-toluenesulphonate, sodium or potassium iodide in formic or acetic acid, lithium iodide in 2,4,6-collidine and borontribromide. Reaction conditions vary widely depending on the dealkylation agent used and the ether to be cleaved. The reaction conditions generally employed when using the above "ether-cleavage" reagents are known in the art and may be adapted without undue experimentation to effect the "ether-cleavage" reactions outlined above.

The hydrolytic cleavage reactions outlined above may be effected using any of the conventional methods known in the art for the hydrolytic cleavage of esters and thioesters. In general hydrolytic cleavage by alkaline hydrolysis is preferred.

Compounds of formula I wherein at least one of A, B, D and E is the group YR or $$\overset{O}{\overset{\|}{C}}YR$$

wherein R is not hydrogen may be prepared from the corresponding compound wherein R is hydrogen by any of the conventional methods known in the art. For example, conventional methods known in the art for the esterification of phenols, thiophenols, carboxylic acids and thiocarboxylic acids and conventional methods known in the art for the etherification of phenols and thiophenols.

Generally speaking the process of the invention is effective in inhibiting the growth of, severely damaging, or killing plants both when the compositions are applied directly to the plants (post-emergence applications) and when the compositions are applied to the soil before the emergence of the plants (pre-emergence application).

The compounds of formula I may be used on their own to inhibit the growth of, severely damage, or kill plants but are preferably used in the process of the invention in the form of a composition comprising a compound of formula I in admixture with a carrier comprising a solid or liquid diluent. Therefore, in still a further embodiment the invention provides plant growth inhibiting, plant damaging, or plant killing compositions comprising a compound of formula I as hereinbefore defined and an inert carrier therefor.

Compositions according to the invention include both dilute compositions, which are ready for immediate use, and concentrated compositions, which require to be diluted before use, usually with water. Preferably the compositions contain from 0.01% to 90% by weight of the active ingredient. Dilute compositions ready for use preferably contain from 0.01 to 2% of active ingredient, while concentrated compositions may contain from 20 to 99% of active ingredient, although from 20 to 70% is usually preferred.

Solid compositions may be in the form of granules, or dusting powders wherein the active ingredient is mixed with a finely divided solid, e.g. kaolin, bentonite, kieselguhr, dolomite, calcium carbonate, talc, powdered magnesia, Fuller's earth and gypsum. They may also be in the form of dispersible powders or grains, comprising a wetting agent to facilitate the dispersion of the powder or grains in liquid. Solid compositions in the form of a powder may be applied as foliar dusts.

Liquid compositions may comprise a solution or dispersion of an active ingredient in water optionally containing a surface-active agent, or may comprise a solution or dispersion of an active ingredient in a water-immiscible organic solvent which is dispersed as droplets in water.

Surface-active agents may be of the cationic, anionic, or non-ionic type. The cationic agents are, for example, quaternary ammonium compounds (e.g. cetyltrimethylammonium bromide). Suitable anionic agents are soaps; salts of aliphatic mono esters of sulphuric acid, for example sodium lauryl sulphate; and salts of sulphonated aromatic compounds, for example sodium dodecylbenzenesulphonate, sodium, calcium, and ammonium lignosulphate, butylnaphthalene sulphonate, and a mixture of the sodium salts of diisopropyl- and triisopropyl-naphthalenesulphonic acid. Suitable non-ionic agents are the condensation products of ethylene oxide with fatty alcohols such as oleyl alcohol and cetyl alcohol, or with alkylphenols such as octyl- or nonyl-phenol or octylcresol. Other non-ionic agents are the partial esters derived from long chain fatty acids and hexitol anhydrides, for example sorbitan monolaurate; the condensation products of the partial ester with ethylene oxide; and the lecithins.

The aqueous solutions or dispersions may be prepared by dissolving the active ingredient in water or an organic solvent optionally containing wetting or dispersing agent(s) and then, when organic solvents are used, adding the mixture so obtained to water optionally containing wetting or dispersing agent(s). Suitable organic solvents include, for example, ethylene dichloride, isopropyl alcohol, propylene glycol, diacetone alcohol, toluene, kerosene, methylnaphthalene, the xylenes and trichloroethylene.

The compositions for use in the form of aqueous solutions or dispersions are generally supplied in the form of a concentrate containing a high proportion of the active ingredient, and the concentrate is then diluted with water before use. These concentrates are usually required to withstand storage for prolonged periods and after such storage, to be capable of dilution with water to form aqueous preparations which remain homogeneous for a sufficient time to enable them to be applied by conventional spray equipment. Concentrates conveniently contain 20–90%, preferably 20–70%, by weight of the active ingredient(s). Dilute preparations ready for use may contain varying amounts of active ingredient(s), depending upon the intended purpose; amounts of 0.01% to 10.0% and preferably 0.1% to 2%, by weight of active ingredient(s) are normally used.

A preferred form of concentrated composition comprises the active ingredient which has been finely divided and which has been dispersed in water in the presence of a surface-active agent and a suspending agent. Suitable suspending agents are hydrophilic colloids and include, for example, polyvinylpyrrolidone and sodium carboxymethylcellulose, and the vegetable gums, for example gum acacia and gum tragancanth. Preferred suspending agents are those which impart thixotropic properties to, and increase the viscosity of the concentrate. Examples of preferred suspending agents include hydrated colloidal mineral silicates, such as montmorillonite, beidellite, nontronite, hectorite, saponite, and saucorite. Bentonite is especially preferred. Other suspending agents include cellulose derivatives and polyvinyl alcohol.

The rate of application of the compounds of the invention will depend on a number of factors including, for example, the compound chosen for use, the identity of the plants whose growth is to be inhibited, the formulation selected for use and whether the compound is to be applied for foliage or root uptake. As a general guide, however, an application rate of from 0.05 to 20 kilograms per hectare is suitable while from 0.1 to 10 kilograms per hectare may be preferred.

In the process of the invention the compounds of formula I show herbicidal activity against a wide variety of plants. Certain of the compounds, for example Nos 14, 25 and 42 show a broad spectrum of activity. Other compounds show selectivity. For example, compounds no 4, 8, 12 and 33 show selectivity for the control of weeds in maize while compounds 23 and 33 show selectivity for the control of weeds in wheat.

Therefore, in yet a still further aspect the invention provides a process for selectively controlling the growth of weeds in crops which process comprises applying to the crop or to the growth medium of the crop a compound of formula I, as hereinbefore defined, in an amount sufficient to severely damage or kill the weeds but insufficient to damage the crop substantially.

It is to be understood that the compositions of this invention may comprise, in addition to one or more compounds of the invention, one or more compounds not of this invention which have biological activity.

The invention is now illustrated by, but by no means limited to, the following examples.

EXAMPLE 1

Preparation of 5-Chloro-2-[3-(4,6-dimethyl-2-pyrimidyloxy)phenoxy]-pyrimidine (5)

A mixture of 2-(3-hydroxyphenoxy)-5-chloropyrimidine (2.22 g), 2-chloro-4,6-dimethylpyrimidine (1.43 g), isobutyl methyl ketone (25 ml) and anhydrous potassium carbonate (1.52 g) was heated under reflux for a period of 48 hours. The reaction mixture was diluted with water and the aqueous mixture was extracted with chloroform. The chloroform extract was dried and the solvent was removed by distillation under reduced pressure to give a pale yellow solid. The solid was recrystallised from ethanol to give the title compound (1.3 g), m.p. 142° C.

EXAMPLE 2

Preparation of 1,3-Bis(5-chloro-2-pyrimidyloxy)benzene (2)

A mixture of 5-chloro-2-(methylsulfonyl)pyrimidine (1.93 g), resorcinol (0.55 g), methyl ethyl ketone (25 ml) and anhydrous potassium carbonate (1.52 g) was heated under reflux for a period of 2 hours. The reaction mixture was diluted with water and the aqueous mixture was extracted with chloroform. The chloroform extract was dried and the solvent was removed by distillation under reduced pressure to give a pale yellow solid. The solid was recrystallised from ethanol to give the title compound (1.24 g), m.p. 120° C.

EXAMPLE 3

The compounds listed in Tables 6a and 6b below and identified by compound no with reference to Tables 1 to 5 inclusive were prepared from the appropriate pyrimidine(s) and the appropriate phenol following the procedure described in Example 1 or Example 2 as indicated. The compounds are characterised by melting point/boiling point (Table 6a) or proton magnetic resonance spectrum (Table 6b).

TABLE 6a

| Compound No | Method Ex. No | m.p. °C. | Compound No | Method Ex.No. | m.p. °C. |
|---|---|---|---|---|---|
| 1 | 2 | 262 | 41 | 2 | 141 |
| 2 | 2 | 120 | 42 | 2 | 138 |
| 4 | 2 | 122 | 43 | 2 | 165–170 |
| 5 | 1 | 142 | 44 | 2 | * |
| 6 | 2 | 136 | 45 | 2 | 134 |
| 7 | 2 | 150 | 46 | 2 | 152 |
| 8 | 2 | 161 | 47 | 2 | 130 |
| 9 | 2 | 162 | 49 | 2 | 137 |
| 10 | 2 | 110 | 51 | 2 | 129 |
| 11 | 2 | 155 | 52 | 2 | 140 |
| 12 | 2 | 171 | 53 | 2 | 128 |
| 13 | 2 | 152 | 55 | 2 | 170 |

TABLE 6a-continued

| Compound No | Method Ex. No | m.p. °C. | Compound No | Method Ex.No. | m.p. °C. |
|---|---|---|---|---|---|
| 14 | 2 | 124 | 57 | 2 | 143 |
| 15 | 2 | 153 | 58 | 2 | 97 |
| 16 | 2 | 190 | 60 | 2 | 154 |
| 17 | 2 | 95 | 61 | 2 | ** |
| 18 | 2 | 208 | 62 | 2 | 168 |
| 19 | 2 | 174 | 63 | 2 | 76 |
| 20 | 2 | 160 | 64 | 2 | 157 |
| 21 | 2 | 105 | 65 | 2 | 97 |
| 25 | 1 | 165 | 66 | 2 | 98 |
| 27 | 2 | 152 | 68 | 2 | |
| 28 | 2 | 116 | 69 | 1 | |
| 31 | 2 | 148 | 70 | 2 | 194-200 |
| 33 | 2 | 110 | 71 | 2 | 150-156 |
| 34 | 2 | 130 | 72 | 2 | 190-193 |
| 37 | 2 | 238 | 73 | 2 | 212-215 |
| 39 | 2 | 112 | 74 | 2 | 73 |
| 75 | 2 | 129 | 78 | 2 | 114 |
| 76 | 1 | 119 | 2 | 90 | |
| 77 | 2 | 146 | 81 | 2 | 142 |

*b.p. 200° C. at 0.1 mm Hg
**Mass spectrometry showed molecular ion M+ at m/e 377

TABLE 6b

| Compound No | Method Ex. No | Partial PMR Spectrum (Chemical Shift in ppm in $CDCl_3$) Pyrimidyl H | Phenyl H | Other H |
|---|---|---|---|---|
| 3 | 2 | 8.6(s) | 7.3-7.8(m) | |
| 22 | 2 | 8.3(s) | 7.3-7.8(m) | |
| 23 | 2 | 8.5(s) | 7.3-7.5(m) | 2.7(q,$CH_2$); 1.3(t,$CH_3$) |
| 24 | 2 | 8.5(s) | 7.2(s) | 2.7(q,$CH_2$); 1.3(t,$CH_3$) |
| 26 | 1 | 8.45(s); 8.55(s) | 7.2-7.4(m) | 2.7(q,$CH_2$); 1.2(t,$CH_3$) |
| 29 | 2 | 8.6(s); 8.65(s) | 7.3-7.8(m) | |
| 30 | 2 | 8.65(d) | 8.1(d); 7.3-7.5(m) | 2.6(s,$CH_3$) |
| 32 | 2 | 8.6(s) | 7.45(m) | 6.0(m), 5.2(m), 3.5(m) allyl |
| 36 | 2 | 8.5(s) | 7.45-7.65(m) | 6.85(s,$CH_3$) |
| 40 | 2 | 8.4(s) | 7.15-7.35(m) | 4.3(m,CH); 3.15(dofd,$CH_2$); 1.7 (d,$CH_3$) |
| 48 | 2 | 8.55(s) | 7.35(m) | 6.0(m), 5.2(m), 3.5(m) allyl |
| 50 | 2 | 8.55(s) | 7.0-7.6(m) | 0.8-2.7(m,$C_{12}H_{25}$) |
| 54 | 2 | 8.55(s) | 7.25-7.7(m) | |
| 59 | 2 | 8.4(s) | 6.9-7.3(m) | 4.9(s,$CH_2$) |
| 67 | 2 | 8.5-8.6(m) | 7.2-7.3(m) | 4.65(d,$CH_2$); 2.35(t,CH) |
| 80 | 1 | 8.5(s); 8.3(s) | 7.1-7.8(m) | |

TABLE 6b-continued

| Compound No | Method Ex. No | Partial PMR Spectrum (Chemical Shift in ppm in $CDCl_3$) Pyrimidyl H | Phenyl H | Other H |
|---|---|---|---|---|
| | | 6.7(s) | | |

EXAMPLE 4

Compositions suitable for use in evaluating pre-emergence and post-emergence herbicidal activity were prepared as follows.

A concentrated composition was prepared by adding 4 parts by weight of the active ingredient to 96 parts by weight of "Lubrol" E (a Registered Trade Mark for a condensation product of alkylphenol with ethylene oxide) and the mixture was ball-milled to produce a stable suspension. The concentrated suspension was then diluted with water to give an aqueous composition suitable for use in the evaluation of the herbicidal activity of the active ingredient.

EXAMPLE 5

The pre-emergent herbicidal activity of the compositions prepared according to Example 4 were assessed by the following procedure.

The seeds of the test species were sprinkled onto the surface of soil in each of five seed boxes and covered with a thin layer of sand. Each of four boxes was then sprayed with a quantity of a composition of the invention and the remaining box was sprayed with an equivalent volume of water for comparison purposes. The boxes were then lightly watered with an overhead spray and placed in a glass house to encourage germination of the seeds. Three weeks later the boxes were removed from the glasshouse and the effect of the treatment was visually assessed. The results are presented in Table 7 wherein the damage to the plants is rated on a scale of 0 to 3 where 0 represents 0 to 25% damage and 3 represents 90 to 100% kill.

The names of the test plants were as follows:

Wh: Wheat
Ot: Wild Oats
Rg: Ryegrass
Jm: Japanese millet
P: Peas
Ip: Ipomea
Ms: Mustard
Sf: Sunflower

TABLE 7

PRE-EMERGENCE HERBICIDAL ACTIVITY

| Compound No | Application Rate (kg/ha) | TEST PLANT Wh | Ot | Rg | Jm | P | Ip | Ms | Sf |
|---|---|---|---|---|---|---|---|---|---|
| 2 | 2 | 3 | 3 | 3 | 3 | 2 | 3 | 3 | 2 |
| 2 | 1 | 0 | 3 | 3 | 3 | 0 | 3 | 3 | 0 |
| 3 | 5 | 1 | 2 | 3 | 3 | 2 | 3 | 3 | 0 |
| 3 | 1 | 0 | 0 | 0 | 1 | 0 | 0 | 0 | 0 |
| 4 | 5 | 3 | 3 | 3 | 3 | 2 | 3 | 3 | 3 |
| 4 | 1 | 3 | 3 | 3 | 3 | 1 | 3 | 3 | 1 |
| 4 | 0.5 | 0 | 0 | 0 | 3+ | 0 | 3 | 3+ | 2 |
| 4 | 0.25 | 0 | 0 | 0 | 2 | 0 | 1 3+ | 2 | |
| 5 | 5 | 0 | 0 | 3 | 3 | 0 | 3 | 3 | 3 |
| 5 | 1 | 0 | 0 | 1 | 3 | 0 | 0 | 1 | 0 |
| 6 | 5 | 0 | 0 | 0 | 3 | 0 | 0 | 0 | 0 |
| 10 | 5 | 2 | 2 | 3 | 3 | 0 | 0 | 0 | 0 |
| 10 | 1 | 0 | 0 | 2 | 3 | 0 | 2 | 2 | 0 |

TABLE 7-continued

| Compound No | Application Rate (kg/ha) | PRE-EMERGENCE HERBICIDAL ACTIVITY TEST PLANT Wh | Ot | Rg | Jm | P | Ip | Ms | Sf |
|---|---|---|---|---|---|---|---|---|---|
| 10 | 0.5 | 0 | 0 | 1 | 2 | 0 | 1 | 0 | 0 |
| 12 | 5 | 3 | 2 | 3 | 3 | 1 | 3 | 3 | 0 |
| 12 | 1 | 3 | 2 | 3 | 3 | 0 | 2 | 3 | 0 |
| 12 | 0.5 | 2 | 2 | 3 | 3 | 0 | 2 | 3 | 0 |
| 14 | 5 | 2 | 3 | 3+ | 3+ | 0 | 3+ | 3+ | 0 |
| 14 | 1 | 2 | 3+ | 3+ | 3+ | 0 | 3+ | 3+ | 0 |
| 16 | 5 | 2 | 0 | 3 | 3 | 0 | 2 | 3 | 0 |
| 23 | 5 | 3+ | 3+ | 3+ | 3+ | 0 | 3+ | 3+ | 0 |
| 23 | 1 | 2 | 2 | 3 | 3+ | 0 | 3+ | 0 | |
| 24 | 5 | 1 | 1 | 1 | 3+ | 0 | 2 | 3 | 0 |
| 25 | 5 | 3+ | 3+ | 3+ | 3+ | 2 | 3+ | 3+ | 3 |
| 25 | 1 | 3+ | 3+ | 3 | 3+ | 0 | 3+ | 3+ | 3+ |
| 25 | 0.5 | 3 | 3+ | 2 | 3+ | 0 | 3+ | 3+ | 3 |
| 26 | 5 | 3 | 3 | 2 | 3+ | 0 | 3+ | 3+ | 3 |
| 26 | 1 | 0 | 1 | 1 | 3 | 0 | 2 | 3 | 0 |
| 27 | 5 | 3 | 3 | 1 | 3+ | 0 | 3+ | 3+ | 0 |
| 28 | 5 | 3 | 3+ | 3+ | 3+ | 2 | 2 | 3 | 0 |
| 28 | 1 | 1 | 1 | 3 | 3+ | 0 | 2 | 2 | 0 |
| 29 | 5 | 1 | 1 | 3 | 3+ | 0 | 0 | 0 | 0 |
| 29 | 1 | 0 | 1 | 3 | 3+ | 0 | 0 | 0 | 0 |
| 32 | 5 | 1 | 0 | 3+ | 3+ | 0 | 3+ | 3+ | 3 |
| 32 | 1 | 0 | 0 | 1 | 3 | 0 | 0 | 2 | 0 |
| 33 | 5 | 2 | 2 | 3+ | 3+ | 0 | 1 | 2 | 0 |
| 33 | 1 | 0 | 0 | 2 | 3+ | 0 | 1 | 0 | 0 |
| 39 | 10 | 2 | 3+ | 3+ | 3+ | 0 | 2 | 3+ | 0 |
| 39 | 5 | 0 | 0 | 2 | 2 | 0 | 3+ | 3+ | 0 |
| 42 | 5 | 3 | 3+ | 3+ | 3+ | 2 | 1 | 3 | 1 |
| 42 | 1 | 0 | 1 | 3 | 3 | 0 | 1 | 3 | 0 |
| 47 | 5 | 3+ | 3+ | 3 | 3+ | 0 | 3+ | 3+ | 0 |
| 47 | 1 | 1 | 0 | 2 | 3+ | 0 | 3 | 3 | 0 |
| 47 | 0.5 | 0 | 0 | 0 | 0 | 0 | 2 | 2 | 0 |
| 49 | 5 | 3 | 3 | 3 | 3+ | 2 | 3+ | 3+ | 3 |
| 49 | 1 | 2 | 1 | 2 3 | 1 | 3 | 1 | 2 | |
| 51 | 5 | 0 | 0 | 3 | 3 | 0 | 0 | 3+ | 0 |
| 54 | 5 | 1 | 2 | 3 | 3 | 0 | 0 | 0 | 0 |
| 75 | 5 | 1 | 2 | 2 | 3 | 0 | 0 | 3 0 | |
| 76 | 5 | 1 | 1 | 2 | 3 | 0 | 0 | 2 | 0 |
| 78 | 10 | 0 | 1 | 1 | 2 | 0 | 0 | 0 | 0 |
| 80 | 10 | 0 | 0 | 3+ | 3 | 0 | 0 | 0 | 0 |

EXAMPLE 6

The post-emergent herbicidal activity of the compositions prepared according to Example 4 was assessed by the following procedure.

The seeds of the test species were sprinkled onto the surface of soil in seed boxes and covered with a thin layer of sand. The boxes were lightly watered with an overhead spray and placed in a glass house for one week to permit germination of the seeds and plant growth to a height of 4 to 5 inches. The boxes were then removed from the glass house and sprayed with a composition of the invention. For comparison purposes at least one box containing one week old seedlings was sprayed lightly with water only. After spraying the boxes were returned to the glass house for a further 3 weeks and the effect of the treatment was visually assessed. The results are presented in Table 8 wherein the damage to the plants is rated on a scale of 0 to 3 where 0 represents 0 to 25% damage, and 3 90 to 100% kill.

The names of the test plants were as follows:

Wh: Wheat
Ot: Wild Oats
Rg: Ryegrass
Jm: Japanese millet
P: Peas
Ip: Ipomea
Ms: Mustard
Sf: Sunflower

TABLE 8

| Compound No | Application Rate (kg/ha) | POST-EMERGENCE HERBICIDAL ACTIVITY TEST PLANT Wh | Ot | Rg | Jm | P | Ip | Ms | Sf |
|---|---|---|---|---|---|---|---|---|---|
| 2 | 2 | 2 | 3 | 3 | 3 | 1 | 3 | 3 | 3 |
| 2 | 1 | 0 | 0 | 1 | 3 | 0 | 0 | 3 | 0 |
| 3 | 5 | 0 | 0 | 1 | 3 | 0 | 0 | 0 | 0 |
| 3 | 1 | 0 | 0 | 0 | 1 | 0 | 0 | 0 | 0 |
| 4 | 5 | 3+ | 3+ | 3+ | 3+ | 3+ | 3+ | 3+ | 3+ |
| 4 | 1 | 3 | 3 | 3 | 3+ | 2 | 3+ | 3+ | 3+ |
| 4 | 0.5 | 3 | 3+ | 3 | 3+ | 0 | 3+ | 3+ | 3+ |
| 4 | 0.25 | 1 | 0 | 0 | 3 | 0 | 3+ | 3+ | 3+ |
| 5 | 5 | 0 | 0 | 3 | 3 | 0 | 3 | 3 | 3 |

TABLE 8-continued

| Compound No | Application Rate (kg/ha) | POST-EMERGENCE HERBICIDAL ACTIVITY TEST PLANT Wh | Ot | Rg | Jm | P | Ip | Ms | Sf |
|---|---|---|---|---|---|---|---|---|---|
| 5 | 1 | 0 | 0 | 1 | 3 | 0 | 0 | 0 | 0 |
| 6 | 5 | 0 | 1 | 3 | 3 | 0 | 3 | 3 | 0 |
| 10 | 5 | 3 | 2 | 3 | 3 | 2 | 3 | 3 | 1 |
| 10 | 1 | 0 | 0 | 1 | 3 | 1 | 3 | 3 | 0 |
| 10 | 0.5 | 0 | 0 | 2 | 3 | 1 | 2 | 2 | 0 |
| 12 | 5 | 0 | 1 | 2 | 3 | 0 | 3 | 2 | 2 |
| 12 | 1 | 0 | 1 | 2 | 3 | 0 | 3 | 2 | 2 |
| 12 | 0.5 | 0 | 0 | 1 | 3 | 0 | 3 | 2 | 1 |
| 14 | 5 | 0 | 2 | 2 | 3+ | 0 | 3 | 2 | 2 |
| 14 | 1 | 0 | 0 | 1 | 3+ | 0 | 0 | 0 | 0 |
| 16 | 5 | 1 | 0 | 2 | 3+ | 1 | 3 | 3 | 0 |
| 23 | 5 | 3+ | 3+ | 3+ | 3+ | 0 | 3+ | 3 | 2 |
| 23 | 1 | 3 | 3 | 3+ | 3+ | 0 | 3+ | 3 | 0 |
| 24 | 5 | 2 | 3+ | 3 | 3+ | 0 | 3+ | 3 | 0 |
| 25 | 5 | 3 | 3 | 2 | 3 | 0 | 3+ | 3 | 3 |
| 25 | 1 | 2 | 0 | 0 | 3 | 0 | 3 | 3 | 2 |
| 26 | 5 | 3 | 3 | 2 | 3+ | 0 | 3+ | 3 | 0 |
| 26 | 1 | 0 | 0 | 0 | 3 | 0 | 3 | 3 | 0 |
| 28 | 5 | 0 | 0 | 1 | 3+ | 0 | 3 | 3+ | 0 |
| 28 | 1 | 0 | 0 | 1 | 3+ | 0 | 2 | 3 | 0 |
| 29 | 5 | 2 | 1 | 3 | 3+ | 1 | 3+ | 3+ | 2 |
| 32 | 5 | 1 | 2 | 3+ | 3+ | 1 | 3+ | 3+ | 3+ |
| 32 | 1 | 0 | 0 | 2 | 3+ | 0 | 3 | 3 | 3+ |
| 33 | 5 | 2 | 3 | 3 | 3 | 0 | 3 | 3 | 2 |
| 33 | 1 | 1 | 2 | 2 | 3 | 0 | 3 | 3 | 2 |
| 42 | 5 | 0 | 0 | 1 | 2 | 0 | 2 | 2 | 2 |
| 42 | 1 | 0 | 0 | 0 | 2 | 0 | 1 | 2 | 2 |
| 47 | 5 | 2 | 3+ | 3+ | 3+ | 0 | 3+ | 3+ | 1 |
| 47 | 1 | 2 | 1 | 3 | 3 | 0 | 3+ | 3+ | 0 |
| 47 | 0.5 | 0 | 0 | 2 | 3 | 0 | 3+ | 3+ | 0 |
| 49 | 5 | 3 | 2 | 2 | 2 | 2 | 3 | 2 | 2 |
| 51 | 5 | 1 | 2 | 2 | 3 | 3+ | 3+ | 3+ | 0 |
| 51 | 1 | 0 | 0 | 0 | 3 | 1 | 3+ | 3+ | 0 |
| 54 | 5 | 0 | 1 | 2 | 3+ | 0 | 3+ | 3+ | 3 |
| 54 | 1 | 0 | 0 | 1 | 3+ | 0 | 3+ | 3 | 1 |
| 59 | 5 | 1 | 0 | 2 | 2 | 1 | 2 | 3 | 0 |
| 75 | 5 | 1 | 1 | 2 | 3 | 0 | 2 | 3 | 3 |
| 76 | 5 | 2 | 2 | 2 | 3 | 0 | 0 | 2 | 3 |
| 78 | 10 | 0 | 0 | 3 | 3+ | 0 | 0 | 3 | 3+ |
| 80 | 10 | 0 | 0 | 1 | 3+ | 0 | 0 | 1 | 2 |

EXAMPLE 7

The compounds were formulated for test by mixing an appropriate amount with 5 ml of an emulsion prepared by diluting 160 ml of a solution containing 21.8 g per liter of "Span" 80 and 78.2 g per liter of "Tween" 20 in methylcyclohexanone to 500 ml with water. "Span" 80 is a Trade Mark for a surface-active agent comprising sorbitan monolaurate. "Tween" 20 is a Trade Mark for a surface-active agent comprising a condensate of sorbitan monolaurate with 20 molar proportions of ethylene oxide. Each 5 ml emulsion containing a test compound was then diluted to 40 ml with water and sprayed onto young pot plants (post-emergence test) of the species named in Table 9 below. Damage to test plants was assesed after 14 days on a scale of 0 to 5 where 0 is 0 to 20% damage and 5 is complete kill. In a test for pre-emergence herbicidal activity, seeds of the test plants were sown in a shallow slit formed in the surface of soil in fibre trays. The surface was then levelled and sprayed, and fresh soil then spread thinly over the sprayed surface. Assessment of herbicidal damage was carried out after 21 days using the same scale of 0 to 5 as in the post-emergence test. In both cases the degree of herbicidal damage was assessed by comparison with untreated control plants. The results are given in Table 9 below. A dash (—) means that no experiment was carried out.

The names of the test plants were as follows:

| | |
|---|---|
| Sb | Sugar beet |
| Rp | Rape |
| Ct | Cotton |
| Sy | Soy bean |
| Mz | Maize |
| Ww | Winter wheat |
| Rc | Rice |
| Sn | *Senecio vulgaris* |
| Ip | *Ipomea purpurea* |
| Am | *Amaranthus retroflexus* |
| Pi | *Polygonum aviculare* |
| Ca | *Chenopodium album* |
| Po | *Portulaca oleracea* |
| Xa | *Xanthium pensylvanicum* |
| Ab | *Abutilon theophrasti* |
| Cv | *Convolulus arvensis* |
| Ot | Cultivated oats and wild oats (*Avena fatua*) Wild oats are used in the post-emergence test and cultivated oats in the pre-emergence test |
| Dg | *Digitaria sunguinalis* |
| Pu | *Poa annua* |
| St | *Setaria viridis* |
| Ec | *Echinochloa crus-galli* |
| Sh | *Sorghum halepense* |
| Ag | *Agropyron repens* |
| Cn | *Cyperus rotundus* |

TABLE 9- PART A

| Compound No | Application Method Rate (kg/ha) | TEST PLANT Sb | Rp | Ct | Sy | Mz | Mw | Rc | Sn | Ip | Am | Pi | Ca |
|---|---|---|---|---|---|---|---|---|---|---|---|---|---|
| 2 | PRE 5 | 5 | 5 | 2 | 5 | 5 | 5 | 4 | 5 | 4 | 5 | 4 | 4 |
| 2 | PRE 1 | 4 | 4 | 0 | 2 | 1 | 1 | 0 | 5 | 0 | 4 | 4 | 4 |
| 2 | POST 5 | 4 | 5 | 4 | 4 | 3 | 4 | 1 | 5 | 4 | 4 | 5 | 5 |
| 2 | POST 1 | 4 | 3 | 1 | 2 | 0 | 0 | 0 | 3 | 2 | 4 | 3 | 4 |
| 4 | PRE 2.5 | 5 | 5 | 5 | 5 | 5 | 5 | 4 | 5 | 4 | 5 | 5 | 5 |
| 4 | PRE 0.25 | 5 | 5 | 5 | 4 | 2 | 4 | 1 | 3 | 4 | 5 | 5 | 4 |
| 4 | PRE 0.125 | 4 | 5 | 3 | 4 | 1 | 3 | 2 | 4 | 1 | 5 | 5 | 4 |
| 4 | POST 2.5 | 4 | 4 | 3 | 4 | 2 | 3 | 3 | 4 | 4 | 4 | 4 | 4 |
| 4 | POST 1 | 3 | 4 | 2 | 4 | 1 | 3 | 2 | 4 | 4 | 4 | 4 | 4 |
| 5 | pre 5 | 4 | 5 | 1 | 3 | 2 | 4 | 1 | 2 | 5 | 5 | 5 | 4 |
| 5 | PRE 1 | 2 | 2 | 1 | 1 | 0 | 1 | 0 | — | 0 | 3 | — | 4 |
| 5 | POST 5 | 4 | 4 | 1 | 4 | 2 | 3 | 2 | 5 | 4 | 4 | 4 | 4 |
| 5 | POST 1 | 2 | 2 | 1 | 2 | 0 | 0 | 0 | 3 | 2 | 5 | — | 3 |
| 10 | PRE 2 | 4 | 4 | 0 | 3 | 1 | 3 | 0 | 4 | 0 | 4 | — | 4 |
| 10 | POST 2 | 4 | 3 | 2 | 3 | 1 | 0 | 0 | 2 | 3 | 5 | 5 | 4 |
| 10 | POST 1 | 4 | 2 | 3 | 2 | 0 | 0 | 0 | 2 | 3 | 5 | 2 | 4 |
| 12 | PRE 1 | 5 | 5 | 5 | 4 | 3 | 5 | — | 0 | 4 | 5 | — | 4 |
| 12 | PRE 0.25 | 5 | 5 | 1 | 3 | 1 | 4 | 2 | 1 | 1 | 5 | — | 4 |
| 12 | POST 1 | 4 | 4 | 0 | 3 | 1 | — | 2 | 1 | 4 | 4 | 4 | 4 |
| 12 | POST 0.5 | 3 | 4 | 0 | 3 | 0 | — | 1 | 1 | 4 | 4 | 4 | 4 |
| 14 | PRE 0.25 | 5 | 5 | 4 | 3 | 0 | 4 | 4 | — | 0 | 2 | — | 5 |
| 14 | POST 0.25 | 5 | 4 | 2 | 4 | 0 | 1 | 1 | 0 | 2 | 2 | 4 | 4 |
| 23 | PRE 1 | 5 | 5 | 3 | 3 | 2 | 3 | 2 | 0 | 2 | 5 | — | 4 |
| 23 | PRE 0.2 | 5 | 5 | 0 | 1 | 0 | 1 | 1 | 0 | 0 | 0 | — | 4 |
| 23 | POST 1 | 3 | 3 | 2 | 2 | 0 | — | 2 | 0 | 2 | 3 | 3 | 4 |
| 24 | PRE 5 | 4 | 5 | 1 | 2 | 2 | 4 | 3 | 0 | 3 | 4 | — | 4 |
| 24 | PRE 1 | 4 | 4 | 1 | 1 | 2 | 1 | 1 | — | 0 | 0 | 0 | 4 |
| 24 | POST 5 | 2 | 4 | 2 | 3 | 1 | — | 3 | 0 | 3 | 4 | 2 | 4 |
| 24 | POST 1 | 3 | 0 | 0 | 4 | 0 | — | 0 | 0 | 1 | 1 | 0 | 4 |
| 25 | PRE 5 | 5 | 5 | 5 | 4 | 5 | 5 | 4 | 5 | 5 | 5 | — | 4 |
| 25 | PRE 1 | 5 | 5 | 5 | 4 | 5 | 5 | 4 | 4 | 4 | 5 | — | 4 |
| 25 | POST 5 | 4 | 4 | 2 | 4 | 2 | — | 4 | 3 | 4 | 4 | 4 | 4 |
| 25 | POST 1 | 4 | 4 | 2 | 4 | 0 | — | 0 | 0 | 4 | 4 | 3 | 4 |
| 26 | PRE 5 | 5 | 5 | 4 | 4 | 4 | 4 | 4 | 0 | 4 | 5 | — | 4 |
| 26 | PRE 1 | 4 | 5 | 1 | 2 | 1 | 2 | 2 | 0 | 1 | 3 | — | 4 |
| 26 | POST 5 | 4 | 4 | 2 | 4 | 2 | — | 4 | 3 | 4 | 4 | 4 | 4 |
| 26 | POST 1 | 2 | 2 | 1 | 2 | 0 | — | 4 | 0 | 2 | 1 | 1 | 4 |
| 27 | PRE 5 | 5 | 5 | 3 | 4 | 2 | 4 | 2 | 0 | 3 | 4 | — | 4 |
| 27 | PRE 1 | 5 | 5 | 2 | 3 | 0 | 4 | 2 | 0 | 0 | 3 | — | 4 |
| 27 | POST 5 | 4 | 4 | 0 | 2 | 1 | — | 4 | 0 | 2 | 2 | 3 | 4 |
| 27 | POST 1 | 3 | 4 | 0 | 3 | 0 | — | 0 | 0 | 2 | 1 | 3 | 4 |
| 28 | PRE 5 | 5 | 5 | 2 | 5 | 5 | 5 | 4 | 3 | 4 | 5 | — | 5 |
| 28 | PRE 1 | 4 | 4 | 0 | 2 | 1 | 1 | 0 | 1 | 0 | 5 | — | 4 |
| 28 | POST 5 | 4 | 4 | 4 | 4 | 4 | 1 | 0 | 3 | 4 | 4 | 4 | 4 |
| 28 | POST 1 | 3 | 3 | 2 | 4 | 1 | 0 | 0 | 2 | 3 | 4 | 2 | 4 |
| 47 | PRE 5 | 4 | 5 | 1 | 4 | 2 | 5 | 4 | 0 | 2 | 5 | — | 4 |
| 47 | PRE 1 | 4 | 5 | — | 1 | 2 | 4 | 2 | 0 | 3 | 5 | — | — |
| 47 | POST 5 | 4 | 4 | 1 | 3 | 1 | 1 | 0 | 1 | 4 | 4 | 4 | 4 |
| 47 | POST 1 | 3 | 4 | 0 | 3 | 1 | 1 | 0 | 1 | 4 | 4 | 3 | 4 |
| 48 | PRE 5 | 3 | 5 | 0 | 1 | 2 | 4 | 2 | 0 | 2 | 5 | — | 3 |
| 48 | POST 5 | 4 | 4 | 3 | 3 | 2 | 2 | 0 | 3 | 4 | 4 | 3 | 4 |
| 48 | POST 1 | 4 | 3 | 0 | 2 | 2 | 0 | 0 | 2 | 4 | 4 | 2 | 4 |
| 49 | PRE 5 | 5 | 5 | 1 | 4 | 4 | 4 | 4 | 5 | 5 | 5 | — | 4 |
| 49 | PRE 0.2 | 4 | 4 | — | 0 | 1 | 0 | 0 | 4 | 0 | 4 | — | 4 |
| 49 | POST 5 | 4 | 4 | 2 | 4 | 3 | 3 | 4 | 4 | 4 | 4 | — | 4 |
| 49 | POST 1 | 4 | 3 | 1 | 4 | 2 | 1 | 3 | 4 | 4 | 4 | — | 4 |
| 51 | PRE 5 | 5 | 5 | 0 | 1 | 1 | 4 | 2 | 0 | 4 | 4 | 4 | — |
| 51 | PRE 1 | 3 | 4 | 2 | 1 | 0 | 1 | 1 | 0 | 0 | 3 | 1 | — |
| 51 | POST 5 | 2 | 4 | 1 | 4 | 1 | 1 | 4 | 0 | 4 | 4 | 4 | 4 |
| 51 | POST 1 | 3 | 4 | 1 | 3 | 0 | 0 | 0 | 0 | 2 | 4 | 1 | 3 |
| 52 | PRE 5 | 5 | 5 | 0 | 4 | 4 | 3 | 2 | 0 | 2 | — | 5 | 5 |
| 52 | PRE 1 | 5 | 5 | 0 | 4 | 2 | 0 | 0 | 0 | 0 | — | 5 | 5 |
| 52 | POST 5 | 4 | 4 | 0 | 4 | 2 | 1 | 0 | 0 | 4 | 4 | 4 | 4 |
| 52 | POST 1 | 4 | 3 | 1 | 4 | 2 | 0 | 0 | 0 | 3 | 4 | 2 | 3 |
| 54 | PRE 5 | 5 | 5 | 4 | 4 | 4 | 5 | 5 | 5 | 4 | — | 5 | 4 |
| 54 | PRE 1 | 4 | 5 | 0 | 3 | 4 | 4 | 2 | 4 | 0 | — | 5 | 4 |
| 54 | POST 5 | 4 | 4 | 4 | 4 | 3 | 2 | 1 | 3 | 4 | 4 | 4 | 4 |
| 54 | POST 1 | 4 | 4 | 2 | 4 | 1 | 0 | 0 | 2 | 2 | 4 | 4 | 4 |
| 76 | PRE 5 | 5 | 5 | 2 | 4 | 4 | 5 | 3 | 4 | — | 5 | — | 4 |
| 76 | PRE 1 | 5 | 5 | 1 | 2 | 1 | 4 | 1 | 4 | — | 5 | — | 4 |
| 76 | POST 5 | 4 | 4 | 0 | 3 | 1 | 2 | 1 | 2 | 0 | 4 | — | 4 |
| 76 | POST 1 | 4 | 3 | 0 | 3 | 0 | 0 | 0 | 2 | 0 | 4 | — | 3 |

TABLE 9 - PART B

| Compound No | Application Method Rate (kg/ha) | TEST PLANT Po | Xa | Ab | Cv | Ot | Dg | Pu | St | Ec | Sh | Ag | Cn |
|---|---|---|---|---|---|---|---|---|---|---|---|---|---|
| 2 | PRE 5 | 5 | 3 | 5 | — | 5 | 5 | 5 | 5 | 5 | 5 | 2 | 3 |
| 2 | PRE 1 | 5 | 0 | 3 | — | 4 | 4 | 3 | 4 | 5 | 0 | 0 | 1 |
| 2 | POST 5 | 5 | 4 | 4 | 5 | 4 | 5 | 5 | 5 | 5 | 3 | 3 | 4 |
| 2 | POST 1 | 4 | 0 | 1 | 4 | 0 | 0 | 0 | 0 | 0 | 0 | 0 | |
| 4 | PRE 2.5 | 5 | 3 | 5 | — | 5 | 5 | 5 | 5 | 5 | 4 | 5 | 1 |
| 4 | PRE 0.25 | 5 | 0 | 5 | — | 5 | 2 | 5 | 5 | 2 | 3 | 3 | 0 |
| 4 | PRE 0.125 | 5 | — | 5 | — | 5 | 3 | 4 | 5 | 3 | 2 | 1 | 0 |
| 4 | POST 2.5 | 3 | 3 | 4 | 4 | 3 | 4 | 4 | 5 | 4 | 3 | 2 | 4 |
| 4 | POST 1 | 4 | 2 | 3 | 4 | 4 | 4 | 4 | 4 | 4 | 3 | 2 | 3 |
| 5 | PRE 5 | 5 | — | 1 | — | 5 | 5 | 5 | 5 | 4 | 4 | 1 | 0 |
| 5 | PRE 1 | 4 | — | 2 | — | 0 | 3 | 3 | 3 | 0 | 0 | 0 | 0 |
| 5 | POST 5 | 4 | 3 | 3 | 4 | 3 | 4 | 4 | 4 | 1 | 2 | 2 | 0 |
| 5 | POST 1 | 5 | 1 | 1 | 2 | 1 | 1 | 1 | 0 | 0 | 0 | 0 | 0 |
| 10 | PRE 2 | 5 | — | 5 | — | 1 | 3 | 4 | 5 | 4 | 2 | 1 | 1 |
| 10 | POST 2 | 5 | — | 3 | 4 | 0 | 5 | 0 | 3 | 1 | 1 | 0 | 0 |
| 10 | POST 1 | 5 | — | 2 | 4 | 0 | 5 | 0 | 1 | 0 | 0 | 0 | 0 |
| 12 | PRE 1 | 5 | 0 | 5 | — | 5 | 4 | 5 | 5 | — | — | 2 | 0 |
| 12 | PRE 0.25 | 5 | 0 | 5 | — | 5 | 3 | 5 | 5 | 5 | 0 | 0 | 0 |
| 12 | POST 1 | 5 | 1 | 4 | 4 | 3 | 4 | 4 | 4 | 4 | 3 | 1 | 0 |
| 12 | POST 0.5 | 4 | 1 | 3 | 4 | 2 | 4 | 3 | 2 | 1 | 3 | 0 | 0 |
| 14 | PRE 0.25 | 4 | — | 5 | — | 5 | 3 | 4 | 4 | 3 | 0 | 0 | 0 |
| 14 | POST 0.25 | 3 | 1 | 3 | 3 | 0 | 0 | 1 | 0 | 0 | 0 | 0 | 0 |
| 23 | PRE 1 | 5 | — | 5 | — | 4 | 4 | 4 | 5 | 5 | 3 | 0 | 0 |
| 23 | PRE 0.2 | 4 | — | 4 | — | 4 | 4 | 0 | 5 | 5 | 4 | 3 | 0 |
| 23 | POST 1 | 3 | 2 | 3 | 2 | 3 | 4 | 3 | 3 | 1 | 1 | 2 | 0 |
| 24 | PRE 5 | 3 | — | 5 | — | 4 | 4 | 4 | 4 | 5 | 4 | 1 | 0 |
| 24 | PRE 1 | 2 | — | 3 | — | 1 | 2 | 3 | 0 | 2 | 0 | 0 | 0 |
| 24 | POST 5 | 3 | 1 | 4 | 2 | 2 | 4 | 3 | 3 | 3 | 1 | 1 | 0 |
| 24 | POST 1 | 2 | 0 | 3 | 0 | 0 | 3 | 1 | 1 | 1 | 0 | 0 | 0 |
| 25 | PRE 5 | 5 | — | 5 | — | 5 | 5 | 5 | 5 | 5 | 5 | 1 | 2 |
| 25 | PRE 1 | 5 | — | 5 | — | 5 | 5 | 5 | 5 | 5 | 5 | 1 | 0 |
| 25 | POST 5 | 4 | 3 | 4 | 3 | 4 | 4 | 4 | 5 | 4 | 4 | 4 | 3 |
| 25 | POST 1 | 4 | 2 | 4 | 2 | 2 | 3 | 4 | 3 | 3 | 2 | 1 | 0 |
| 26 | PRE 5 | 4 | — | 5 | — | 5 | 4 | 5 | 5 | 5 | 5 | 1 | 0 |
| 26 | PRE 1 | 2 | — | 4 | — | 3 | 4 | 4 | 3 | 4 | 2 | 1 | 0 |
| 26 | POST 5 | 4 | 3 | 4 | 4 | 4 | 5 | 4 | 4 | 4 | 2 | 1 | 0 |
| 26 | POST 1 | 2 | 1 | 3 | 1 | 2 | 4 | 3 | 2 | 0 | 0 | 0 | 0 |
| 27 | PRE 5 | 3 | — | 5 | — | 5 | 4 | 4 | 4 | 5 | 4 | 1 | 0 |
| 27 | PRE 1 | 2 | — | 5 | — | 5 | 4 | 4 | 4 | 4 | 3 | 0 | 0 |
| 27 | POST 5 | 3 | 0 | 3 | 3 | 3 | 4 | 4 | 4 | 4 | 2 | 0 | 0 |
| 27 | POST 1 | 3 | 0 | 3 | 1 | 0 | 4 | 2 | 1 | 1 | 0 | 0 | 0 |
| 28 | PRE 5 | 5 | 1 | 5 | — | 5 | 5 | 5 | 5 | 5 | 5 | 2 | 3 |
| 28 | PRE 1 | 5 | 0 | 4 | — | 0 | 4 | 5 | 5 | 4 | 3 | 1 | 0 |
| 28 | POST 5 | 4 | 2 | 4 | 4 | 3 | 4 | 4 | 5 | 2 | 3 | 0 | 1 |
| 28 | POST 1 | 4 | 0 | 4 | 3 | 0 | 1 | 2 | 4 | 1 | 0 | 0 | 0 |
| 47 | PRE 5 | 4 | 0 | 5 | — | 5 | 5 | 5 | 5 | 5 | 4 | 1 | 0 |
| 47 | PRE 1 | 4 | 0 | 4 | — | 4 | 4 | 5 | 4 | 4 | 2 | 0 | 0 |
| 47 | POST 5 | 5 | 3 | 4 | 4 | 3 | 3 | 4 | 5 | 4 | 1 | 2 | 0 |
| 47 | POST 1 | 5 | 2 | 3 | 4 | 2 | 3 | 4 | 3 | 3 | 1 | 2 | 0 |
| 48 | PRE 5 | 5 | 0 | 4 | — | 4 | 4 | 5 | 4 | 4 | 3 | 0 | 0 |
| 48 | POST 5 | 5 | 3 | 4 | 4 | 3 | 4 | 4 | 5 | 3 | 3 1 | 0 | |
| 48 | POST 1 | 5 | 1 | 4 | 3 | 1 | 3 | 2 | 5 | 4 | 2 | 0 | 0 |
| 49 | PRE 5 | 5 | 3 | 5 | — | 5 | 5 | 5 | 5 | 5 | 5 | 3 | 3 |
| 49 | PRE 0.2 | 4 | — | 2 | — | 2 | 2 | 3 | 2 | 0 | 2 | 0 | 2 |
| 49 | POST 5 | 4 | — | 4 | 4 | 4 | 4 | 5 | 4 | 4 | 3 | 1 | 0 |
| 49 | POST 1 | 3 | — | 3 | 4 | 2 | 2 | 4 | 4 | 2 | 0 | 0 | 0 |
| 51 | PRE 5 | 3 | 0 | 4 | — | 4 | 4 | 5 | 4 | 4 | 3 | 0 | 0 |
| 51 | PRE 1 | 1 | 0 | 3 | — | 3 | 2 | 4 | 2 | 2 | 0 | 0 | 0 |
| 51 | POST 5 | 4 | 1 | 4 | 2 | 0 | 1 | 3 | 2 | 1 | 0 | 0 | 0 |
| 51 | POST 1 | 4 | 0 | 4 | 2 | 0 | 0 | 2 | 0 | 0 | 0 | 0 | 0 |
| 52 | PRE 5 | 4 | 0 | 4 | — | 0 | 4 | 4 | 5 | 4 | 1 | 0 | 0 |
| 52 | PRE 1 | 4 | 0 | 4 | — | 0 | 3 | 4 | 4 | 4 | 0 | 0 | 0 |
| 52 | POST 5 | — | 0 | 2 | 4 | 0 | 2 | 2 | 2 | 1 | — | 0 | 1 |
| 52 | POST 1 | — | 1 | 2 | 3 | 0 | 0 | 0 | 2 | 0 | — | 0 | 0 |
| 54 | PRE 5 | 5 | 0 | 5 | — | 5 | 5 | 5 | 5 | 5 | 4 | 0 | 0 |
| 54 | PRE 1 | 4 | 0 | 4 | — | 0 | 4 | 4 | 5 | 4 | 1 | 0 | 0 |
| 54 | POST 5 | — | 4 | 4 | 4 | 2 | 4 | 1 | 4 | 3 | — | 0 | 3 |
| 54 | POST 1 | — | 2 | 4 | 4 | 0 | 2 | 1 | 2 | 1 | — | 0 | 0 |
| 76 | PRE 5 | 5 | 2 | 4 | — | 5 | 5 | 5 | 4 | 5 | 4 | 3 | 0 |
| 76 | PRE 1 | 5 | 0 | 4 | — | 5 | 4 | 5 | 3 | 5 | 3 | 1 | 0 |
| 76 | POST 5 | 4 | — | 3 | 0 | 4 | 4 | 4 | 4 | 4 | 1 | 0 | 0 |
| 76 | POST 1 | 4 | — | 3 | 0 | 1 | 0 | 3 | 5 | 1 | 0 | 0 | 0 |

EXAMPLE 8

This Example illustrates the selective herbicidal activity of compounds of the invention.

The compounds were formulated for test by mixing an appropriate amount with 5 ml of an emulsion prepared by diluting 160 ml of a solution containing 21.8 g per liter of "Span" 80 and 78.2 g per liter of "Tween" 20 in methylcyclohexanone to 500 ml with water. "Span" 80 is a Trade Mark for a surface-active agent comprising sorbitan monolaurate. "Tween" 20 is a Trade Mark for a surface-active agent comprising a condensate of sorbitan monolaurate with 20 molar proportions of ethylene oxide. Each 5 ml emulsion containing a test compound was then diluted to 40 ml with water and sprayed on to young pot plants (post-emergence test) of the species named in Table 10 below. Damage to test plants was assessed after 26 days on a scale of 0 to 9 where 0 is 0 to 10% damage and 9 is complete kill. In preemergence test the seeds of the test plants were sown in a shallow slit formed in the surface of soil in fibre trays. The surface was then levelled and sprayed with the test composition and fresh soil was spread thinly over the sprayed surface. Assessment of herbicidal damage was carried out after 26 days using the same 0 to 9 scale used in the post-emergence test. In both cases the degree of herbicidal damage was assessed by comparison with untreated control plants and the results are given in Table 10 below. A dash (—) means that no experiment was carried out.

TABLE 10 - PART A

| Compound No | Application Method Rate (kg/ha) | TEST PLANTS | | | | | | | | | | |
|---|---|---|---|---|---|---|---|---|---|---|---|---|
| | | Ww | Av | Al | Bt | Ag | Ga | Sm | Ca | Pi | Tm | Sp |
| 19 | PRE 4 | 1 | 5 | 7 | 5 | 2 | 7 | 9 | 8 | — | 6 | 9 |
| 19 | PRE 2 | 1 | 3 | 7 | 7 | 3 | 6 | 9 | 5 | — | 4 | 7 |
| 19 | PRE 1 | 0 | 1 | 5 | 3 | 0 | 5 | 8 | 3 | — | 3 | 2 |
| 23 | PRE 0.5 | 0 | 0 | 6 | 7 | 3 | 6 | 9 | 7 | — | 6 | 6 |
| 23 | POST 2 | 3 | 3 | 4 | 9 | 7 | 7 | 9 | 9 | 9 | 0 | 8 |
| 23 | POST 1 | 0 | 1 | 3 | 8 | 7 | 5 | 8 | 8 | 7 | 0 | 9 |
| 23 | POST 0.5 | 0 | 0 | 2 | 2 | 1 | 6 | 8 | 8 | 6 | 0 | 6 |
| 33 | POST 1 | 0 | 5 | 5 | 0 | 5 | 7 | 7 | 8 | 8 | 0 | 9 |
| 33 | POST 0.5 | 0 | 2 | 1 | 2 | 2 | 7 | 5 | 8 | 6 | 0 | 9 |

The names of the test plants were as follows:
Ww Winter wheat
Av *Avena fatua*
Al *Alopecurus myosuroides*
Bt *Bromus tectorum*
Ag *Agropyron repens*
Ga
Sm *Stellaria media*
Ca *Chenopodium album*
Pi *Polygonum aviculare*
Tm *Tripleurospermum maritimum*
Sp *Sinapis alba*

TABLE 10 - PART B

| Compound No | Application Method Rate (Kg/ha) | TEST PLANT | | | | | | | | | | | |
|---|---|---|---|---|---|---|---|---|---|---|---|---|---|
| | | Mz | Am | Ip | Ab | Se | Si | Ds | Ec | Dg | St | Sh | Pm |
| 4 | PRE 0.5 | 0 | 9 | 9 | 9 | 9 | 9 | 9 | 7 | 9 | 8 | 8 | 9 |
| 4 | PRE 0.125 | 0 | 9 | 8 | 9 | 7 | 9 | 9 | 4 | 9 | 6 | 7 | 9 |
| 4 | POST 0.125 | 0 | 9 | 3 | 8 | 7 | 5 | 5 | 1 | 0 | 0 | 0 | 3 |
| 6 | PRE 2 | 0 | 9 | 8 | 9 | 9 | 9 | 9 | 8 | 9 | 9 | 8 | 9 |
| 6 | PRE 1 | 0 | 9 | 7 | 9 | 3 | 9 | 9 | 2 | 9 | 6 | 2 | 6 |
| 8 | POST 2 | 0 | 8 | 8 | 9 | 9 | 7 | 9 | 7 | 9 | 9 | 7 | 8 |
| 8 | POST 1 | 0 | 6 | 6 | 9 | 9 | 6 | 7 | 6 | 9 | 9 | 3 | 6 |
| 12 | PRE 0.5 | 0 | 9 | 7 | 9 | 9 | 9 | 9 | 8 | 9 | 9 | 8 | 9 |
| 12 | PRE 0.25 | 0 | 9 | 7 | 9 | 8 | 9 | 9 | 4 | 9 | 9 | 2 | 6 |
| 12 | PRE 0.125 | 0 | 9 | 1 | 9 | 4 | 9 | 8 | 1 | 8 | 3 | 0 | 6 |
| 12 | POST 0.5 | 0 | 9 | 4 | 9 | 9 | 6 | 7 | 3 | 0 | 5 | 1 | 1 |
| 19 | PRE 2 | 0 | 6 | 7 | 8 | 4 | 9 | — | 6 | 8 | 9 | 7 | 8 |
| 19 | PRE 1 | 0 | 3 | 2 | 8 | 3 | 8 | — | 4 | 6 | 8 | 4 | 7 |
| 23 | PRE 0.5 | 0 | 0 | 5 | 9 | 7 | 9 | — | 8 | 9 | 7 | 7 | 7 |
| 27 | PRE 2 | 0 | 2 | 5 | 8 | 5 | 9 | — | 8 | 9 | 8 | 7 | 7 |
| 33 | POST 0.5 | 0 | 5 | 4 | 8 | 8 | 7 | 8 | 0 | 1 | 1 | 0 | 0 |
| 33 | POST 0.25 | 0 | 6 | 3 | 9 | 8 | 8 | 9 | 1 | 0 | 2 | 1 | 0 |

The names of the test plants were as follows:
Mz Maize
Am *Amaranthus retroflexus*
Ip *Ipomea purpurea*
Ab *Abutilon theophrasti*
Se *Sesbania exaltata*
Si *Sida spinosa*
Ds *Datura stramonium*
Ec *Echinochloa crus-galli*
Dg *Digitaria sanguinalis*
St *Setaria viridis*
Sh *Sorghum halepense*
Pm *Panicum maximum*

We claim:

1. A process of inhibiting the growth of, severely damaging, or killing plants which process comprises applying to the plant or the growth medium thereof an effective amount of a composition comprising as active ingredient a compound of formula I:

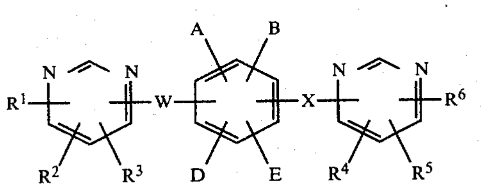

I wherein:

$R^1$, $R^2$, $R^3$, $R^4$, $R^5$ and $R^6$ are independently chosen from the group consisting of hydrogen, halogen, nitro, cyano, thiocyano, carboxy and sulfo; $C_1$ to $C_6$ alkyl, $C_2$ to $C_6$ alkenyl, $C_1$ to $C_6$ alkoxy, $C_2$ to $C_6$ alkenyloxy, $C_2$ to $C_6$ alkynyloxy and $C_1$ to $C_6$ alkylthio wherein each group is optionally substituted with one or more substituents chosen from halogen, phenyl, hydroxy, and $C_1$ to $C_6$ alkoxy; $C_3$ to $C_7$ cycloalkyl optionally substituted with one or two $C_1$ to $C_4$ alkyl groups; $NR^7R^8$ wherein $R^7$ and $R^8$ are independently chosen from hydrogen, $C_1$ to $C_6$ alkyl, $C_2$ to $C_6$ alkanoyl, phenyl and benzoyl; $NR^9R^{10}R^{11}]^{\oplus}X^{\ominus}$ wherein $X^{\ominus}$ is an anion and $R^9$, $R^{10}$ and $R^{11}$ are chosen independently from $C_1$ to $C_6$ alkyl optionally substituted with one or two substituents chosen from halogen, phenyl, hydroxy and $C_1$ to $C_6$ alkoxy, and phenyl optionally substituted with one or two substituents chosen from halogen, $C_1$ to $C_6$ alkyl, $C_1$ to $C_6$ alkoxy, nitro and cyano; $C_1$ to $C_6$-(alkoxy)carbonyl; $C_1$ to $C_6$-(alkoxy)sulfonyl; carbamoyl and sulfamoyl optionally substituted on the amide nitrogen with one or two groups chosen from $C_1$ to $C_6$ alkyl and phenyl optionally substituted with one or two substituents chosen from halogen, $C_1$ to $C_6$ alkyl, $C_1$ to $C_6$ alkoxy, nitro and cyano; and phenyl optionally substituted with one or two substituents chosen from halogen, $C_1$ to $C_6$ alkyl, $C_1$ to $C_6$ alkoxy, nitro and cyano;

A, B, D and E are independently chosen from the group consisting of hydrogen, halogen, nitro, cyano, thiocyano and sulfo; $C_1$ to $C_{12}$ alkyl and $C_2$ to $C_6$ alkenyl wherein each group is optionally substituted with one or two substituents chosen from halogen, phenyl, hydroxy, $C_2$ to $C_6$ alkoxycarbonyl and $C_1$ to $C_6$ alkoxy; $C_3$ to $C_7$ cycloalkyl optionally substituted with one or two $C_1$ to $C_4$ alkyl groups; $C_2$ to $C_6$ alkylcarbonyl; $NR^7R^8$ and $NR^9R^{10}R^{11}]^{\oplus}X^{\ominus}$ wherein $R^7$, $R^8$, $R^9$, $R^{10}$, $R^{11}$ and $X^{\ominus}$ are as hereinbefore defined; phenyl optionally substituted with one or two substituents chosen from halogen, $C_1$ to $C_6$ alkyl, $C_1$ to $C_6$ alkoxy, nitro and cyano; carbamoyl and sulfamoyl optionally substituted on the amide nitrogen with one or two groups chosen from $C_1$ to $C_6$ alkyl and phenyl optionally substituted with one or two substituents chosen from halogen, $C_1$ to $C_6$ alkyl, $C_1$ to $C_6$ alkoxy, nitro and cyano; $C_1$ to $C_6$ (alkoxy)sulfonyl; a 1,3-butadienylene group wherein two adjacent substituents chosen from A, B, D and E form a bridging group; and the groups YR and

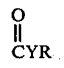

wherein:

Y is chosen from oxygen and sulfur and R is chosen from the group consisting of hydrogen; $C_1$ to $C_{10}$ alkyl, $C_2$ to $C_{10}$ alkenyl and $C_2$ to $C_{10}$ alkynyl wherein each group is optionally substituted with one or two substituents chosen from halogen, phenyl, hydroxy and $C_1$ to $C_6$ alkoxy; $C_3$ to $C_7$ cycloalkyl optionally substituted with one or two $C_1$ to $C_4$ alkyl groups; $C_1$ to $C_6$ alkanoyl; benzoyl optionally substituted on the phenyl ring with one or two substituents chosen from halogen, nitro, cyano, $C_1$ to $C_6$ alkyl and $C_1$ to $C_6$ alkoxy; phenyl optionally substituted with one or two substituents chosen from halogen, $C_1$ to $C_6$ alkyl, $C_1$ to $C_6$ alkoxy, nitro and cyano; the cation of an inorganic base such as, for example, an alkali metal ion or an alkaline earth metal ion; the cation of an organic base such as, for example an ammonium ion $NR^{12}R^{13}R^{14}R^{15}]^{\oplus}$ wherein $R^{12}$, $R^{13}$, $R^{14}$ and $R^{15}$ are independently chosen from the group hydrogen, $C_1$ to $C_6$ alkyl, $C_1$ to $C_6$ hydroxyalkyl, phenyl and benzyl; and the groups

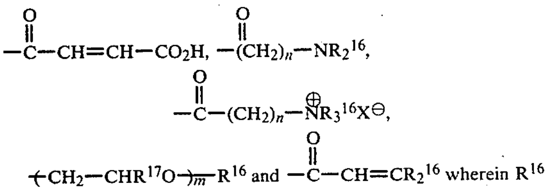

wherein $R^{16}$ is hydrogen or a $C_1$ to $C_6$ alkyl group, $R^{17}$ is hydrogen or methyl, n is an integer from 2 to 6, m is an integer from 2 to 20 and $X^{\oplus}$ is an anion; and W and X are independently chosen from oxygen and sulfur.

2. A process according to claim 1 wherein in the compound of formula I:

$R^1$, $R^2$, $R^3$, $R^4$, $R^5$ and $R^6$ are independently chosen from the group consisting of hydrogen, halogen, nitro, cyano, $C_1$ to $C_6$ alkyl, $C_2$ to $C_6$ alkenyl, $C_1$ to $C_6$ haloalkyl and phenyl optionally substituted with halogen;

A, B, D and E are independently chosen from the group consisting of hydrogen, halogen, nitro, cyano, formyl, carbamoyl, $C_1$ to $C_{12}$ alkyl, $C_1$ to $C_6$ haloalkyl, $C_2$ to $C_6$ alkenyl optionally substituted with $C_2$ to $C_6$ alkoxycarbonyl, $C_2$ to $C_6$ alkylcarbonyl, OR wherein R is chosen from $C_1$ to $C_6$ alkyl, $C_2$ to $C_6$ alkenyl, $C_2$ to $C_6$ alkynyl and the groups phenyl and benzyl wherein in each group the phenyl ring is optionally substituted with one or two substituents independently chosen from nitro and halogen; or two adjacent substituents chosen from A, B, D and E form a 1,3-butadienylene bridging group; and W and X are independently chosen from oxygen and sulfur.

3. A process according to claim 2 wherein in the compound of formula I:

$R^1$, $R^2$, $R^3$, $R^4$, $R^5$ and $R^6$ are independently chosen from the group consisting of hydrogen, halogen, $C_1$ to $C_6$ alkyl, $C_1$ to $C_6$ haloalkyl and phenyl optionally substituted with halogen;

A, B, D and E are independently chosen from the group consisting of hydrogen, halogen, nitro, cyano, carbamoyl, $C_1$ to $C_6$ alkyl, $C_1$ to $C_6$ haloalkyl, $C_2$ to $C_6$ alkenyl, $C_2$ to $C_6$ alkylcarbonyl and OR wherein R is chosen from $C_1$ to $C_6$ alkyl, $C_2$ to $C_6$ alkenyl, $C_2$ to $C_6$ alkynyl, and phenyl optionally substituted with one or two nitro groups; and W and X are both oxygen.

4. A process according to claim 1 wherein in the compound of formula I the pyrimidyl rings are linked through the 2- or 4-position to the phenyl ring in a structure of formula II

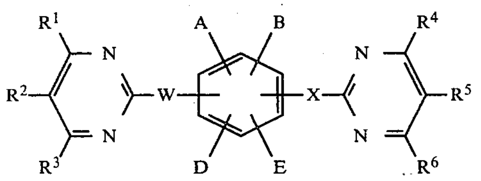

II, a structure of formula III

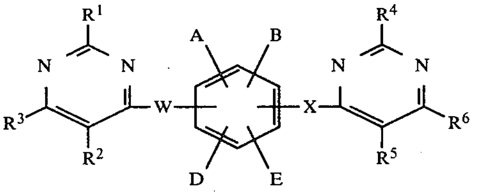

III, or a structure of formula IV

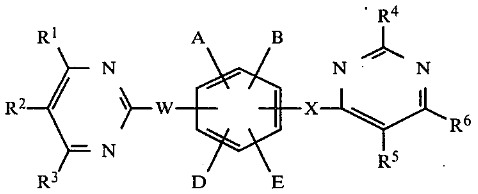

IV.

5. A process according to claim 4 wherein in the compound of formula I the pyrimidyl rings are linked through the 2-position to the phenyl ring in a structure of formula IIa

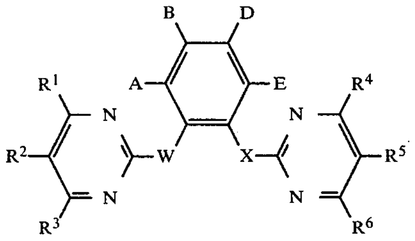

IIa, or a structure of formula IIb

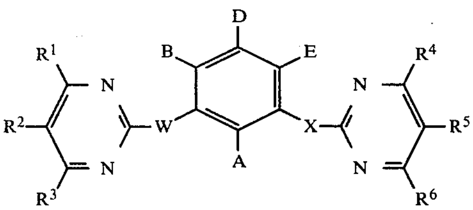

IIb.

6. A process according to claim 5 wherein in the compounds of formula IIa and IIb:

$R^1$, $R^2$, $R^3$, $R^4$, $R^5$ and $R^6$ are independently chosen from hydrogen, methyl and halogen;

two of A, B, D and E are hydrogen and two of A, B, D and E are independently chosen from hydrogen, halogen nitro, methyl, ethyl, allyl, methoxy and 4-chlorobenzyloxy; and W and X are both oxygen.

7. A process according to claim 6 wherein in the compounds of formula IIa and IIb:

$R^1$, $R^3$, $R^4$ and $R^6$ are each hydrogen and $R^2$ and $R^5$ are independently chosen from chlorine and bromine;

three of A, B, D and E are hydrogen and one of A, B, D and E is chosen from hydrogen, chlorine, nitro, methyl, ethyl, allyl, methoxy and 4-chlorobenzyloxy; and W and X are both oxygen.

8. A process according to claim 1 for selectively controlling the growth of weeds in crops.

9. A process according to claim 1 wherein the compound of formula I is applied at a rate in the range from 0.01 to 20 kilograms per hectare.

10. A process according to claim 9 wherein the rate is in the range from 0.1 to 10 kilograms per hectare.

11. A compound of formula I:

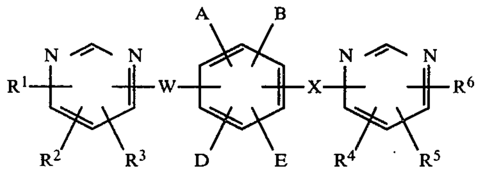

I wherein:

$R^1$, $R^2$, $R^3$, $R^4$, $R^5$ and $R^6$ are independently chosen from the group consisting of hydrogen, halogen, nitro, cyano, thiocyano, carboxy and sulfo; $C_1$ to $C_6$ alkyl, $C_2$ to $C_6$ alkenyl, $C_1$ to $C_6$ alkoxy, $C_2$ to $C_6$ alkenyloxy, $C_2$ to $C_6$ alkynyloxy and $C_1$ to $C_6$ alkylthio wherein each group is optionally substituted with one or more substituents chosen from halogen, phenyl, hydroxy, and $C_1$ to $C_6$ alkoxy; $C_3$ to $C_7$ cycloalkyl optionally substituted with one or two $C_1$ to $C_4$ alkyl groups; $NR^7R^8$ wherein $R^7$ and $R^8$ are independently chosen from hydrogen, $C_1$ to $C_6$ alkyl, $C_2$ to $C_6$ alkanoyl, phenyl and benzoyl; $NR^9R^{10}R^{11}]^{\oplus}X^{\ominus}$ wherein $X^{\ominus}$ is an anion and $R^9$, $R^{10}$ and $R^{11}$ are chosen independently from $C_1$ to $C_6$ alkyl optionally substituted with one or two substituents chosen from halogen, phenyl, hydroxy and $C_1$ to $C_6$ alkoxy, and phenyl optionally substituted with one or two substituents chosen from halogen, $C_1$ to $C_6$ alkyl, $C_1$ to $C_6$ alkoxy, nitro and cyano; $C_1$ to $C_6$-(alkoxy)carbonyl; $C_1$ to $C_6$-(alkoxy)sulfonyl; carbamoyl and sulfamoyl optionally substituted on the amide nitrogen with one or two groups chosen from $C_1$ to $C_6$ alkyl and phenyl optionally substituted with one or two substituents chosen from halogen, $C_1$ to $C_6$ alkyl, $C_1$ to $C_6$ alkoxy, nitro and cyano; and phenyl optionally substituted with one or two substituents chosen from halogen, $C_1$ to $C_6$ alkyl, $C_1$ to $C_6$ alkoxy, nitro and cyano;

A, B, D and E are independently chosen from the group consisting of hydrogen, halogen, nitro, cyano, thiocyano and sulfo; $C_1$ to $C_{12}$ alkyl and $C_2$ to $C_6$ alkenyl wherein each group is optionally substituted with one or two substituents chosen from halogen, phenyl, hydroxy, $C_2$ to $C_6$ alkoxycarbonyl and $C_1$ to $C_6$ alkoxy; $C_3$ to $C_7$ cycloalkyl optionally substituted with one or two $C_1$ to $C_4$ alkyl groups; $C_2$ to $C_6$ alkylcarbonyl; $NR^7R^8$ and $NR^9R^{10}R^{11}]^{\oplus}X^{\ominus}$ wherein $R^7$, $R^8$, $R^9$, $R^{10}$, $R^{11}$ and $X^{\ominus}$ are as hereinbefore defined; phenyl optionally substituted with one or two substituents chosen from halogen, $C_1$ to $C_6$ alkyl, $C_1$ to $C_6$ alkoxy, nitro and cyano; carbamoyl and sulfamoyl optionally substituted on the amide nitrogen with one or two groups chosen from $C_1$ to $C_6$ alkyl and phenyl optionally substituted with one or two substituents chosen from halogen, $C_1$ to $C_6$ alkyl, $C_1$ to $C_6$ alkoxy, nitro and cyano; $C_1$ to $C_6$ (alkoxy)sulfonyl; a 1,3-butadienylene group wherein two adjacent substituents chosen from A, B, D and E form a bridging group; and the groups YR and

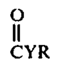

wherein:

Y is chosen from oxygen and sulfur and R is chosen from the group consisting of hydrogen; $C_1$ to $C_{10}$ alkyl, $C_2$ to $C_{10}$ alkenyl and $C_2$ to $C_{10}$ alkynyl wherein each group is optionally substituted with one or two substituents chosen from halogen, phenyl, hydroxy and $C_1$ to $C_6$ alkoxy; $C_3$ to $C_7$ cycloalkyl optionally substituted with one or two $C_1$ to $C_4$ alkyl groups; $C_1$ to $C_6$ alkanoyl; benzoyl optionally substituted on the phenyl ring with one or two substituents chosen from halogen, nitro, cyano, $C_1$ to $C_6$ alkyl and $C_1$ to $C_6$ alkoxy; phenyl optionally substituted with one or two substituents chosen from halogen, $C_1$ to $C_6$ alkyl, $C_1$ to $C_6$ alkoxy, nitro and cyano; the cation of an inorganic base such as, for example, an alkali metal ion or an alkaline earth metal ion; the cation of an organic base such as, for example an ammonium ion $NR^{12}R^{13}R^{14}R^{15}]^{\oplus}$ wherein $R^{12}$, $R^{13}$, $R^{14}$ and $R^{15}$ are independently chosen from the group hydrogen, $C_1$ to $C_6$ alkyl, $C_1$ to $C_6$ hydroxyalkyl, phenyl and benzyl; and the groups

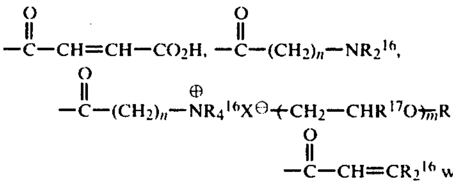
and
wherein $R^{16}$ is hydrogen or a $C_1$ to $C_6$ alkyl group, $R^{17}$ is hydrogen or methyl, n is an integer from 2 to 6, m is an integer from 2 to 20 and $X^{\ominus}$ is an anion; and W and X are independently chosen from oxygen and sulfur.

12. A compound according to claim 11 wherein:

$R^1$, $R^2$, $R^3$, $R^4$, $R^5$ and $R^6$ are independently chosen from the group consisting of hydrogen, halogen, nitro, cyano, $C_1$ to $C_6$ alkyl, $C_2$ to $C_6$ alkenyl, $C_1$ to $C_6$ haloalkyl and phenyl optionally substituted with halogen;

A, B, D and E are independently chosen from the group consisting of hydrogen, halogen, nitro, cyano, formyl, carbamoyl, $C_1$ to $C_{12}$ alkyl, $C_1$ to $C_6$ haloalkyl, $C_2$ to $C_6$ alkenyl optionally substituted with $C_2$ to $C_6$ alkoxycarbonyl, $C_2$ to $C_6$ alkylcarbonyl, OR wherein R is chosen from $C_1$ to $C_6$ alkyl, $C_2$ to $C_6$ alkenyl, $C_2$ to $C_6$ alkynyl and the groups phenyl and benzyl wherein in each group the phenyl ring is optionally substituted with one or two substituents independently chosen from nitro and halogen; or two adjacent substituents chosen from A, B, D and E form a 1,3-butadienylene bridging group; and W and X are independently chosen from oxygen and sulfur.

13. A compound according to claim 12 wherein:

$R^1$, $R^2$, $R^3$, $R^4$, $R^5$ and $R^6$ are independently chosen from the group consisting of hydrogen, halogen, $C_1$ to $C_6$ alkyl, $C_1$ to $C_6$ haloalkyl and phenyl optionally substituted with halogen;

A, B, D and E are independently chosen from the group consisting of hydrogen, halogen, nitro, cyano, carbamoyl, $C_1$ to $C_6$ alkyl, $C_1$ to $C_6$ haloalkyl, $C_2$ to $C_6$ alkenyl, $C_2$ to $C_6$ alkylcarbonyl and OR wherein R is chosen from $C_1$ to $C_6$ alkyl, $C_2$ to $C_6$ alkenyl, $C_2$ to $C_6$ alkynyl, and phenyl optionally substituted with one or two nitro groups; and W and X are both oxygen.

14. A compound according to claim 11 wherein in the compound of formula I the pyrimidyl rings are linked through the 2- or 4-position to the phenyl ring in a structure of formula II

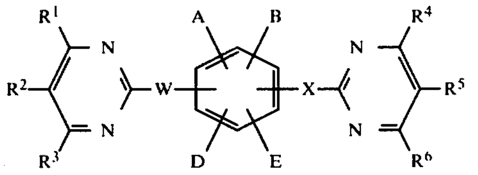
II, a structure of formula III

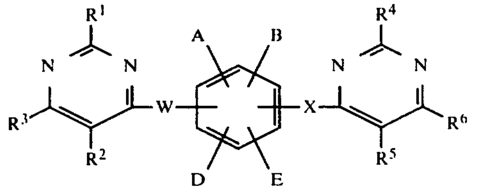
III, or a structure of formula IV

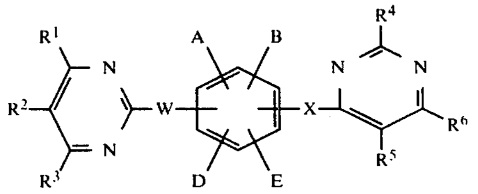
IV.

15. A compound according to claim 14 wherein in the compound of formula II the pyrimidyl rings are linked through the 2-position to the phenyl ring in a structure of formula IIa

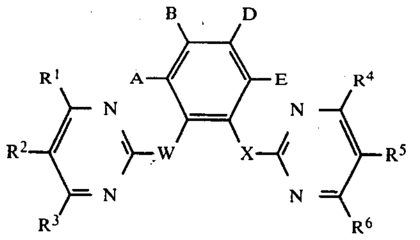

IIa, or a structure of formula IIb

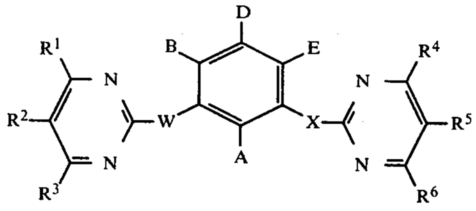

IIb.

16. A compound according to claim 15 wherein in the compounds of formula IIa and IIb:

$R^1$, $R^2$, $R^3$, $R^4$, $R^5$ and $R^6$ are independently chosen from hydrogen, methyl and halogen;

two of A, B, D and E are hydrogen and two of A, B, D and E are independently chosen from hydrogen, halogen nitro, methyl, ethyl, allyl, methoxy and 4-chlorobenzyloxy; and W and X are both oxygen.

17. A compound according to claim 16 wherein in the compounds of formula IIa and IIb:

$R^1$, $R^3$, $R^4$ and $R^6$ are each hydrogen and $R^2$ and $R^5$ are independently chosen from chlorine and bromine;

three of A, B, D and E are hydrogen and one of A, B, D and E is chosen from hydrogen, chlorine, nitro, methyl, ethyl, allyl, methoxy and 4-chlorobenzyloxy; and W and X are both oxygen.

18. A herbicidal composition comprising as active ingredient a compound of formula I as defined according to claim 11 and a carrier therefor.

19. A composition according to claim 18 wherein the composition is in the form of a liquid and comprises a surface active agent.

20. A composition according to claim 18 wherein the composition is in the form of a powder.

21. A dilute composition according to claim 18 which comprises from 0.01 to 2% by weight of active ingredient.

22. A concentrated composition according to claim 18 which comprises from 20 to 90% by weight of active ingredient.

* * * * *